US010258376B2

(12) United States Patent
Dillard et al.

(10) Patent No.: US 10,258,376 B2
(45) Date of Patent: Apr. 16, 2019

(54) MEDICAL DEVICES AND SYSTEMS FOR MANIPULATING FOREIGN BODIES AND METHODS OF USING THE SAME

(71) Applicant: SPIRATION, INC., Redmond, WA (US)

(72) Inventors: David H. Dillard, Grapeview, WA (US); Clinton L. Finger, Bellevue, WA (US); Erik Liljegren, Kirkland, WA (US); Desmond O'Connell, Lake Forest Park, WA (US); Richard O. Shea, Kenmore, WA (US); William A. Sirokman, Kirkland, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 14/498,493

(22) Filed: Sep. 26, 2014

(65) Prior Publication Data

US 2015/0080903 A1    Mar. 19, 2015

Related U.S. Application Data

(63) Continuation of application No. PCT/US2013/031077, filed on Mar. 13, 2013.
(Continued)

(51) Int. Cl.
*A61B 17/50*    (2006.01)
*A61B 17/00*    (2006.01)
*A61B 17/12*    (2006.01)
*A61F 2/01*    (2006.01)
*A61M 25/00*    (2006.01)
*A61M 25/04*    (2006.01)

(52) U.S. Cl.
CPC ........ *A61B 17/50* (2013.01); *A61B 17/00234* (2013.01); *A61B 17/12104* (2013.01); *A61B 17/12172* (2013.01); *A61F 2/01* (2013.01); *A61B 2017/00296* (2013.01); *A61B 2017/12054* (2013.01); *A61F 2002/011* (2013.01); *A61M 25/0082* (2013.01); *A61M 25/04* (2013.01)

(58) Field of Classification Search
CPC ......... A61F 2002/011; A61M 25/0082; A61M 25/04
See application file for complete search history.

(56) References Cited

U.S. PATENT DOCUMENTS 6,071,263 A * 6/2000 Kirkman ........... A61M 25/0082
                                                 604/104
6,156,055 A * 12/2000 Ravenscroft ........... A61B 17/50
                                                 606/127
(Continued)

*Primary Examiner* — Diane Yabut

(57) ABSTRACT

A tool for manipulating a foreign body (e.g., a deployed medical device) can include an operative portion. The operative portion can be used to move the foreign body in the proximal and/or distal directions with respect to the removal/repositioning tool and/or the tissue surrounding the foreign body. In some embodiments, the tool can include a compressing portion that can be used to compress the foreign body as the foreign body is pulled by the operative portion in the proximal direction. The tool can further include a sleeve that can be used to transition the operative portion and/or compressing portion between an opened configuration and a closed configuration. In some embodiments, the tool can be used in conjunction with an endoscope to navigate the tool to the site of a foreign body within the body of a patient.

14 Claims, 16 Drawing Sheets

Related U.S. Application Data

(60) Provisional application No. 61/617,572, filed on Mar. 29, 2012.

(56) References Cited

U.S. PATENT DOCUMENTS

| | | | |
|---|---|---|---|
| 2003/0181945 A1* | 9/2003 | Opolski | A61B 34/72 606/206 |
| 2006/0184193 A1* | 8/2006 | Lowe et al. | 606/200 |
| 2006/0212042 A1* | 9/2006 | Lamport | A61B 17/221 606/108 |
| 2008/0033451 A1* | 2/2008 | Rieber | A61B 17/00234 606/114 |

* cited by examiner

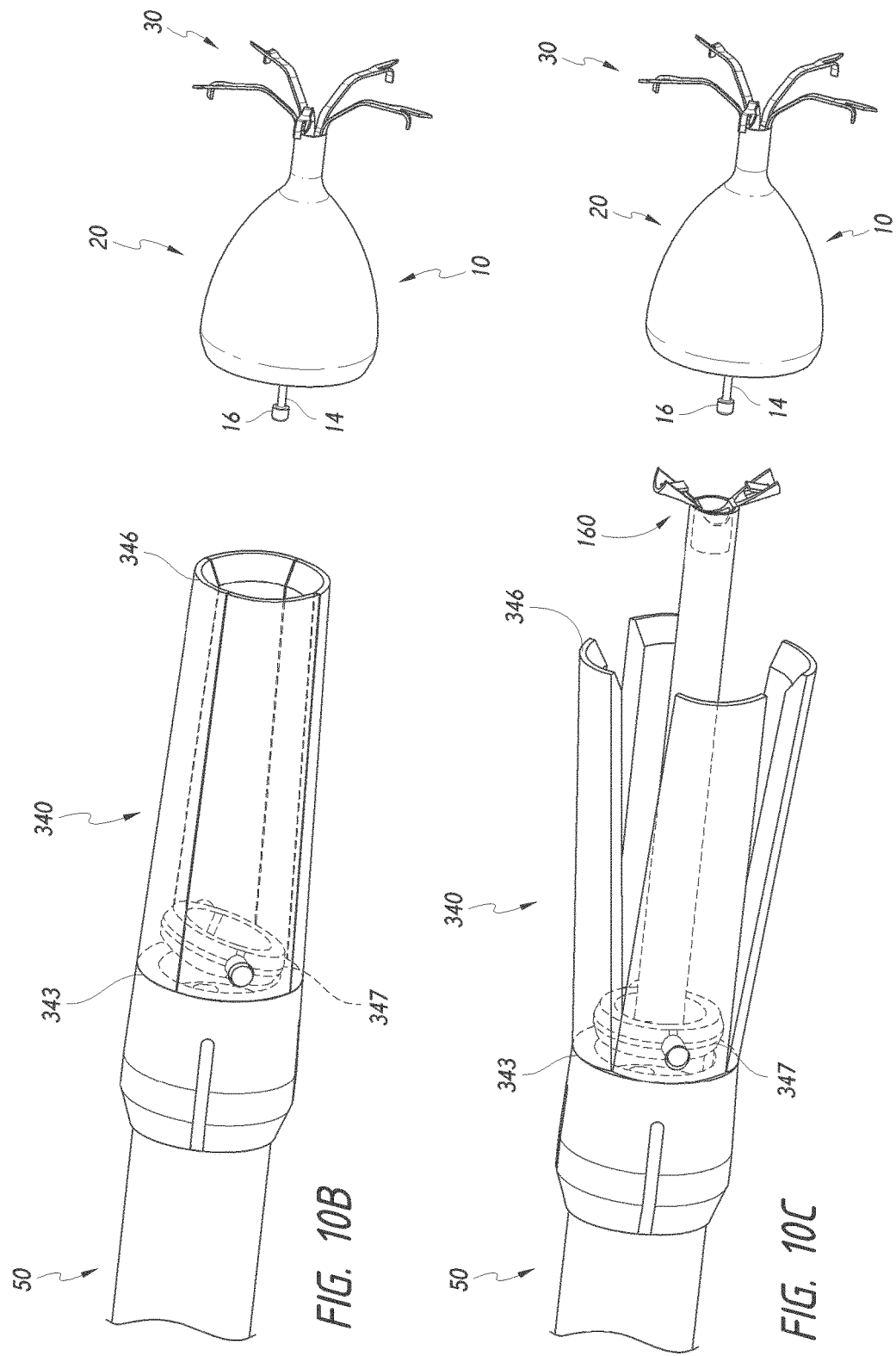

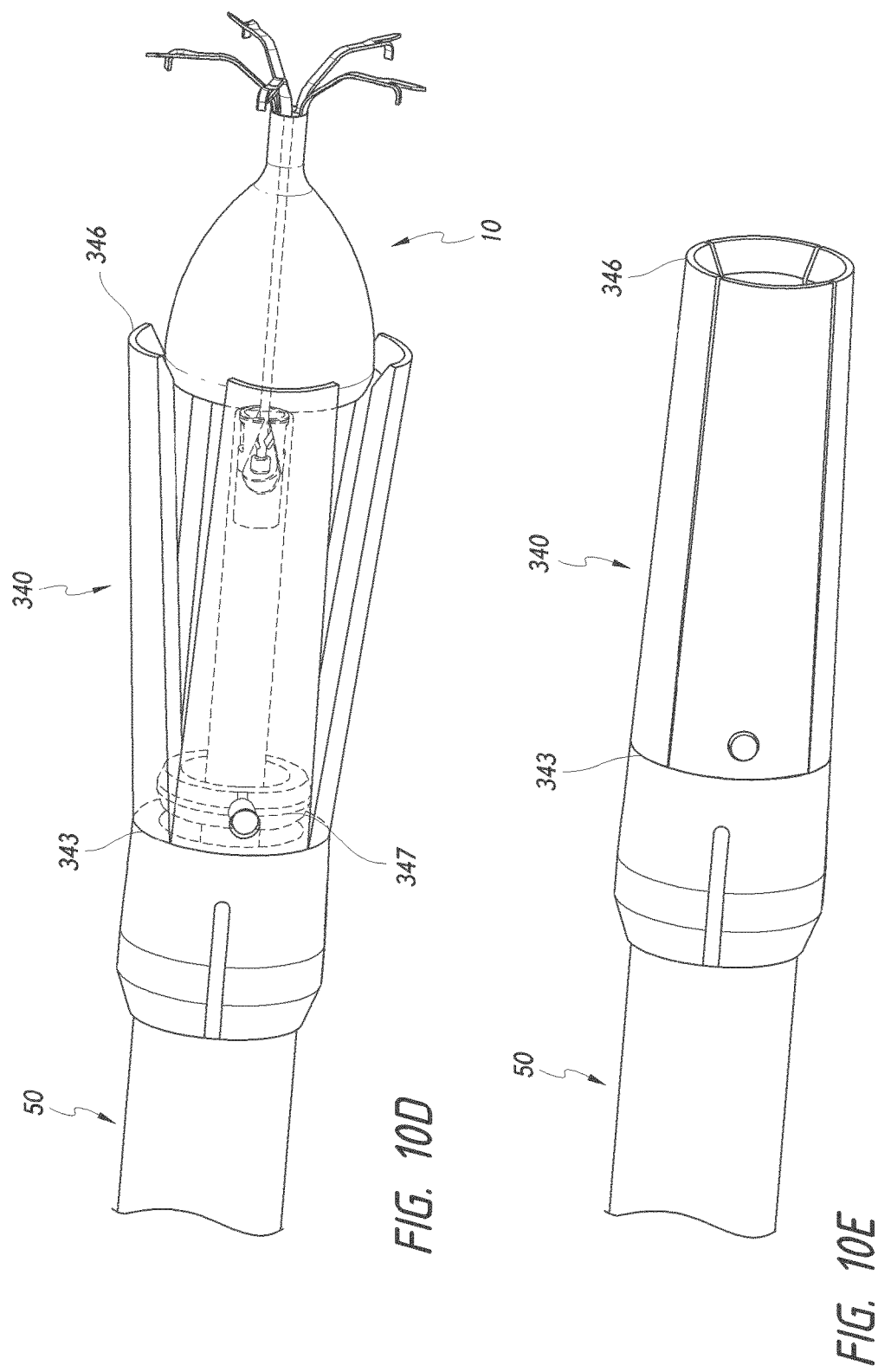

MEDICAL DEVICES AND SYSTEMS FOR MANIPULATING FOREIGN BODIES AND METHODS OF USING THE SAME

RELATED APPLICATIONS

This application claims the benefit under 35 U.S.C. § 120 and 35 U.S.C. § 365(c) as a continuation of International Application No. PCT/US2013/031077, designating the United States, with an international filing date of Mar. 13, 2013, titled MEDICAL DEVICES AND SYSTEMS FOR MANIPULATING FOREIGN BODIES AND METHODS OF USING THE SAME, which claims the benefit of U.S. Provisional Application No. 61/617,572, titled MEDICAL DEVICES AND SYSTEMS FOR MANIPULATING FOREIGN BODIES AND METHODS OF USING THE SAME, filed Mar. 29, 2012, which is hereby incorporated by reference herein in its entirety. Any and all priority claims identified in the Application Data Sheet, or any correction thereto, are hereby incorporated by reference under 37 CFR 1.57.

BACKGROUND

Technical Field

Embodiments of the disclosed devices generally relate to the field of medical devices, and in particular, to methods, systems, and devices for removing and/or repositioning medical devices.

Description of the Related Art

Implantation of medical devices (e.g. medical valve) has proven effective in the treatment of Chronic Obstructive Pulmonary Disease (COPD). Such devices can include the medical devices disclosed in U.S. Pat. Nos. 6,293,951, 6,592,594, 6,722,360, 6,929,637, 7,533,671, 7,691,151, 7,875,048 and U.S. Patent Publication Nos. 2003/0154988, 2003/0181922, 2003/0195385, and 2003/0212412, which are hereby incorporated by reference herein in their entireties.

In some procedures, it is desirable to remove and/or reposition a foreign body within the body or a patient. For example, it may be desirable to remove or reposition a medical device after it has been deployed within a patient's body. In some situations, the implanted device may be surrounded by hyperplasia. In some procedures, it is desirable that a removal and/or repositioning tool be configured to compress the medical device being removed or repositioned without significantly damaging the device. In some procedures, repositioning medical devices, as opposed to removing them, can save time and money for the patient and physician as the desire for a replacement device may be reduced or eliminated.

SUMMARY

According to some embodiments, a tool useful for removing and/or repositioning a foreign body (e.g., a medical device) within a patient's body can include a sleeve member. The sleeve member can have a proximal end, a distal end, and a central axis. The sleeve member can have a tubular body defining an interior lumen and, in some embodiments, can be movable in the proximal and distal directions.

In some embodiments, the tool can include an operative portion having a proximal end, a distal end, and a central axis. The central axis of the operative portion can be generally coaxial with the central axis of the sleeve member. In some embodiments, the operative portion can include a stabilizing portion having a proximal end and a distal end. Furthermore, the operative portion can include a plurality of engagement members, each engagement member having a proximal end and a distal end. The plurality of engagement members can be connected to the stabilizing portion and can extend in the distal direction from the distal end of the stabilizing portion. The engagement members can be configured to transition between an opened configuration and a closed configuration in response to a force applied on the engagement members. The distal ends of the engagement members can be configured to move away from the central axis of the operative portion when transitioning from the closed configuration to the opened configuration. In some embodiments, the operative portion can include one or more grasping portions located on the stabilizing portions. The grasping portions can extend from the engagement members toward the central axis of the operative portion when the engagement members are in the closed configuration.

In some embodiments, the tool can include a compressing portion having a proximal end, a distal end, and a central axis generally coaxial with the central axis of the sleeve member. The compressing portion can be movable in the proximal end distal directions. In some embodiments, the compressing portion is configured to transition between an expanded configuration and a compressed configuration. The compressing portion can be configured to flare outward from the central axis of the compressing portion such that the distal end of the compressing portion is located further from the central axis of the compressing portion than the proximal end of the compressing portion when the compressing portion is in the expanded configuration.

In some embodiments, the sleeve member and operative portion are configured to be housed within a working channel of an endoscope or other deployment device. In some embodiments, the compressing portion is configured to be housed within a working channel of an endoscope of other deployment device. In some embodiments, at least a portion of the operative portion is housed within the interior lumen of the sleeve member. In some embodiments, the sleeve member is configured to be movable in the proximal and distal directions with respect to the operative portion. In some embodiments, the sleeve member is configured to be movable in the proximal and distal directions with respect to the compressing portion. In some embodiments, the operative portion is configured to be movable in the proximal and distal directions with respect to the compressing portion.

In some embodiments of the tool, the engagement members are biased to the opened configuration. In some embodiments, the compressing portion is biased to the expanded configuration. In some embodiments, the engagement members are configured to transition from the opened configuration to the closed configuration when the distal end of the sleeve member is moved from proximal to the proximal ends of the engagement members to lateral or distal to the distal ends of the engagement members.

In some embodiments, the operative portion comprises indentations located at the proximal ends of the engagement members, the indentations configured to reduce the force required to transition the engagement members between the opened configuration and the closed configuration. In some embodiments, the compressing portion comprises a hollow conical, frustoconical, fluted, or trumpeted piece of material. In some embodiments, the compressing portion comprises a plurality of overlapping panels. In some embodiments, the compressing portion has an opening through the compressing portion, the opening configured to allow for visualization through the compressing portion. In some embodiments, the sleeve member comprises a plurality of secondary conduits, wherein each of the secondary conduits has a proximal end and a distal end. In some variants, the compressing portion comprises a plurality of compression wires, wherein at least a portion of each of the compression wires is housed within the plurality of secondary conduits. Each of the compression wires has a proximal end and a distal end and can be configured to transition between an expanded configuration and a compressed configuration. In some embodiments, the compression wires can have a flattened shape.

A method of removing a foreign body (e.g., a medical device) from a deployed location within the body can include using an endoscope or other delivery device to position the tool in a location near and proximal to a foreign body (e.g., a deployed medical device). The method can also include transitioning the engagement members to the opened configuration and the compressing portion to the expanded configuration. In some embodiments, the method can include positioning the operative portions such that a portion of the foreign body is within the engagement members in the opened configuration.

The method can further include transitioning the engagement members to the closed configuration such that the grasping portions grasp the foreign body. The method can include pulling the medical device in the proximal direction and transitioning the compressing portion to the compressed configuration. The method can include capturing at least a portion of the foreign body within the sleeve member, compressing portion, or working channel of the endoscope or other delivery device and moving the tool to a second location within or outside the body.

In some embodiments, the method can further include transitioning the compressing portion to the opened configuration, pushing the foreign body in the distal direction until the medical device is released from the compressing portion, sleeve member and working channel, transitioning the engagement members to the opened configuration, and moving the tool away from the foreign body. In some embodiments, the foreign body is a deployed medical device.

In some embodiments, a tool for repositioning or removing a foreign body within the body of a patient includes a capture portion having a proximal end, a distal end, and a central axis. The capture portion can include a body portion having a proximal end and a distal end. The body portion can be located on the proximal end of the capture portion and the proximal end of the body portion can be configured to removably connect to an endoscope. The capture portion can also include a plurality of compression members, each of the compression members having a proximal end and a distal end. The proximal end of each of the compression members can be rotationally connected to the distal end of the body portion. The compression members can be configured to transition between a closed configuration and an opened configuration upon the application of a force upon the compression members. The distal end of each compression member can be configured to move away from the central axis of the capture portion as the compression member transitions from the closed configuration to the opened configuration. In some embodiments, the capture portion includes an operative portion configured to transition between a closed configuration and an opened configuration. The operative portion can be configured to grasp a portion of the foreign body when the operative portion is transitioned from the opened configuration to the closed configuration while a portion of the foreign body is within the operative portion. The operative portion can further be configured to be housed within a working channel of the endoscope. In some embodiments, the foreign body can be a deployed medical device.

A tool for removing and/or repositioning a foreign body within the body of a patient, the tool can comprise: a sleeve member, the sleeve member having a proximal end, a distal end, and a central axis, the sleeve member comprising a tubular body defining an interior lumen, the sleeve member movable in the proximal and distal directions; an operative portion, the operative portion having a proximal end and a distal end and a central axis generally coaxial with the central axis of the sleeve member, the operative portion comprising: a stabilizing portion, the stabilizing portion having a proximal end and a distal end; a plurality of engagement members, each engagement member having a proximal end and a distal end, the plurality of engagement members connected to the stabilizing portion and extending in the distal direction from the distal end of the stabilizing portion, the engagement members configured to transition between an opened configuration and a closed configuration in response to force applied on the engagement members, the distal ends of the engagement members configured to move away from the central axis of the operative portion when transitioning from the closed configuration to the opened configuration; and one or more grasping portions located on the stabilizing portions, the grasping portions extending from the engagement members toward the central axis of the operative portion when the engagement members are in the closed configuration.

In some embodiments, the tool can further comprise a compressing portion having a proximal end and distal end and a central axis generally coaxial with the central axis of the sleeve member, the compressing portion movable in the proximal and distal directions, the compressing portion configured to transition between an expanded configuration and a compressed configuration, the compressing portion further configured to flare outward from the central axis of the compressing portion such that the distal end of the compressing portion is located further from the central axis of the compressing portion than the proximal end of the compressing portion when the compressing portion is in the expanded configuration.

According to some variants, the engagement members are removable from the stabilizing portion. In some embodiments, the stabilizing portion comprises a groove. The tool can, in some variants, further comprise a band, the plurality of engagement members each being attached to the band. The band can be configured to removably engage with the groove. In some embodiments, the sleeve member and operative portion are configured to be housed within a working channel of an endoscope or other deployment device. The compressing portion can be configured to be housed within a working channel of an endoscope or other deployment device. In some embodiments, at least a portion of the operative portion is housed within the interior lumen of the sleeve member. According to some variants, the sleeve member is configured to be movable in the proximal and distal directions with respect to the operative portion. In some embodiments, the sleeve member is configured to be movable in the proximal and distal directions with respect to the compressing portion. The operative portion can be configured to be movable in the proximal and distal directions with respect to the compressing portion. In some embodiments, the engagement members are biased to the opened configuration. The compressing portion can be biased to the opened configuration. According to some variants, the engagement members are configured to transition from the opened configuration to the closed configuration when the distal end of the sleeve member is moved from proximal to the proximal ends of the engagement members to lateral or distal to the distal ends of the engagement members. The operative portion can comprises indentations located at the proximal ends of the engagement members, the indentations configured to reduce the force required to transition the engagement members between the opened configuration and the closed configuration. In some embodiments, the compressing portion comprises a solid conical piece of material. In some embodiments, the compressing portion comprises a plurality of overlapping spiral panels. The compressing portion can comprise an opening through the compressing portion, the opening configured to allow for visualization through the compressing portion. In some embodiments, the sleeve member comprises a plurality of secondary conduits, wherein each of the secondary conduits has a proximal end and a distal end. According to some variants, the tool comprises a compressing portion, the compressing portion comprising a plurality of compression wires, wherein at least a portion of each of the compression wires is housed within the plurality of secondary conduits, each of the compression wires having a proximal end and a distal end, the compression wires configured to transition between an expanded configuration and a compressed configuration. The compression wires can have a flattened shape. In some embodiments, a gap is formed between the plurality of engagement members over at least a portion of the axial length of the engagement members when the engagement members are in the closed configuration. The foreign body can comprise an extended portion and a central axis such that, when the central axis of the foreign body is not aligned with the central axis of the operative portion, the extended portion can pass through the gap formed between the engagement members and the grasping portions can grasp the sides of the extended portion. In some embodiments, the foreign body is a deployed medical device.

A method of removing a foreign body from a location within the body of a patient using the tool described above can comprise: using an endoscope or other delivery device to position the tool in a location near and proximal to a foreign body; transitioning the engagement members to the opened configuration; positioning the operative portion such that a portion of the foreign body is within the engagement members in the opened configuration; transitioning the engagement members to the closed configuration such that the grasping portions grasp the foreign body; pulling the foreign body in the proximal direction; capturing at least a portion of the foreign body within the sleeve member or working channel of the endoscope or other delivery device; and moving the tool to a second location within or outside the body. In some embodiments, the method comprises: pushing the foreign body in the distal direction until the foreign body is released from the sleeve member and working channel; transitioning the engagement members to the opened configuration; and moving the tool away from the foreign body. According to some variants, the method comprises capturing the entire foreign body within the sleeve member or working channel of the endoscope or other delivery device such that the patient's tissue is substantially protected from contact with the foreign body during repositioning or removal of the foreign body. In some embodiments, the foreign body is a deployed medical device.

A tool for repositioning or removing a foreign body within the body of a patient can comprise: a capture portion having a proximal end and a distal end and a central axis, the capture portion comprising: a body portion having a distal end and a proximal end, the body portion located on the proximal end of the capture portion, the proximal end of the body portion configured to removably connect to an endoscope; one or more compression members, each of the one or more compression members having a proximal end and a distal end, the proximal end of each of the compression members connected to the distal end of the body portion; and an operative portion configured to transition between a closed configuration and an opened configuration, the operative portion further configured to grasp a portion of the foreign body when the operative portion is transitioned from the opened configuration to the closed configuration while a portion of the foreign body is within the operative portion, the operative portion further configured to be housed within a working channel of the endoscope. The one or more compression members can be configured to transition between a closed configuration and an opened configuration upon the application of a force upon the one or more compression members, the distal end of each compression member being configured to move away from the central axis of the capture portion as the compression member transitions from the closed configuration to the opened configuration. According to some embodiments, the foreign body can be a deployed medical device.

A method of removing a foreign body from a location within the body of a patient can comprise: providing a tool comprising: a capture portion having a proximal end and a distal end and a central axis, the capture portion comprising: a body portion having a distal end and a proximal end, the body portion located on the proximal end of the capture portion, the proximal end of the body portion configured to removably connect to an endoscope; one or more compression members, each of the one or more compression members having a proximal end and a distal end, the proximal end of each of the compression members connected to the distal end of the body portion; and an operative portion configured to transition between a closed configuration and an opened configuration, the operative portion further configured to grasp a portion of the foreign body when the operative portion is transitioned from the opened configuration to the closed configuration while a portion of the foreign body is within the operative portion, the operative portion further configured to be housed within a working channel of the endoscope; using an endoscope or other delivery device to position the tool in a location near and proximal to a foreign body; transitioning the compression members to an opened configuration; positioning the operative portion such that a portion of the foreign body is within the operative portion in the opened configuration; transitioning the operative portion to the closed configuration such that the operative portions grasps the foreign body; pulling the foreign body in the proximal direction; capturing at least a portion of the foreign body within compression members; transitioning the compression members to a closed configuration; and moving the tool to a second location within or outside the body.

BRIEF DESCRIPTION OF THE DRAWINGS

Various embodiments are depicted in the accompanying drawings for illustrative purposes, and the drawings should in no way be interpreted as limiting the scope of the embodiments. In addition, various features of one or more disclosed embodiments can be combined to form additional embodiments, which are part of this disclosure.

FIG. 10B is a view of the tool of FIG. 10A attached to the distal end of an endoscope.

FIG. 10C is a view of the tool of FIG. 10A in an expanded configuration.

FIG. 10D is a view of the tool of FIG. 10A partially-engaged with a medical device.

FIG. 10E is a view of the tool of FIG. 10A having a medical device loaded therein.

DETAILED DESCRIPTION

Devices and methods for repositioning within, and/or removing medical devices from, a patient now will be described with reference to the accompanying figures of one or more embodiments. The terminology used in the description presented herein is not intended to be interpreted in any limited or restrictive manner. Rather, the terminology is simply being utilized in conjunction with a detailed description of the embodiments of the devices and methods. For example, although reference is made to the removal and/or repositioning of medical valves within the body, this disclosure is not necessarily limited to medical valves. For instance, embodiments of the present disclosure may be used to remove and/or reposition implantable medical devices or medical devices accessed via or useable within, passages, vessels, cavities, lumens or the like (e.g., stents, plugs, ports, etc.). Furthermore, embodiments may comprise several novel features, no single one of which is solely responsible for its desirable attributes or is believed to be essential to practicing the methods and devices described herein. Although some embodiments described herein refer to removing and/or repositioning a medical device deployed in an airway, this disclosure is not so limited. For example, disclosed devices and methods can be used to remove medical devices from other vessels, passages, cavities and lumens in humans and animals. Additionally, in some embodiments, the removal and/or repositioning device can comprise a plurality of components that can be configured to connect to and/or disconnect from each other.

Additionally, throughout the specification, claims, and drawings, the term "proximal" means nearest the person or persons using the device, and "distal" means furthest from that person or those persons.

Figure 1:
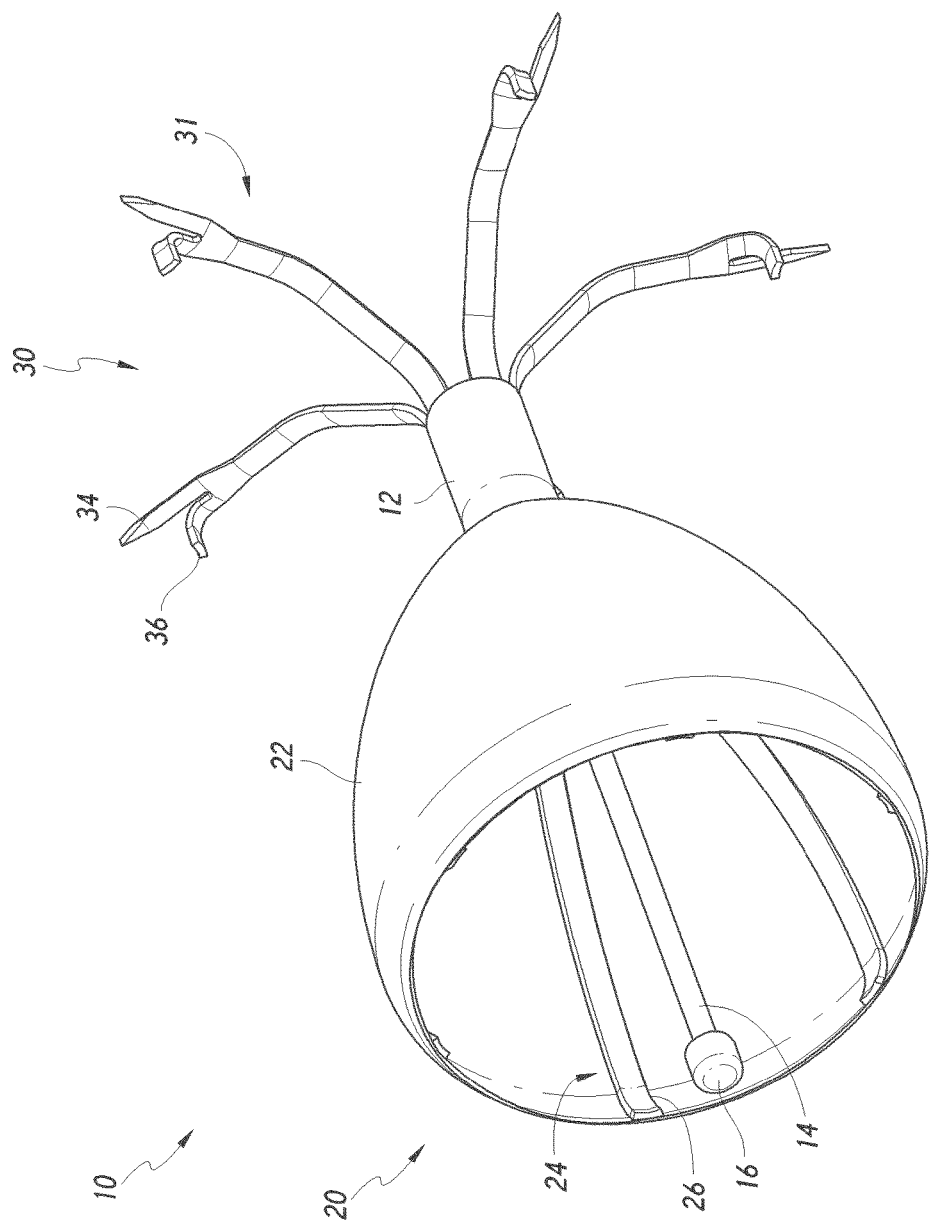
FIG. 1 is a perspective view of a medical valve.

FIG. 1 illustrates an embodiment of a removable medical device 10. In some embodiments, a removable medical device 10 can comprise a valve portion 20. In some embodiments, the valve portion 20 can connect to a hub 12. The valve portion 20 can have one or more struts 24 extending from the hub 12. In some embodiments, the valve portion 20 has a membrane portion 22. The membrane portion 22 can be configured to extend across the one or more struts 24. In some embodiments, the membrane portion 22 can extend across the outside (e.g., the side further from a central axis of the medical device 10) of the one or more struts 24. In some embodiments, the membrane portion 22 can extend across the inside of the one or more struts 24. In some embodiments, the ends of the struts 24 opposite the hub 12 can include turned portions 26. In some embodiments, the turned portions 26 are turned toward the central axis of the medical device 10. In some embodiments, the turned portions 26 are turned away from the central axis of the medical device 10.

In some embodiments, the removable medical device 10 can include a central rod 14. The rod 14 can be positioned along the central axis of the medical device 10. The rod 14 can be configured to attach to the hub 12. In some embodiments, the rod 14 extends in the same direction from the hub 12 as the valve portion 20. In some embodiments, the rod 14 extends in a direction from the hub 12 opposite the valve portion 20. In some embodiments, the rod 14 can have a cap 16 on the end of the rod 14 opposite the hub 12. In some embodiments, the rod 14 and/or cap 16 extend beyond the end of the valve portion 20 opposite the hub 12. In some embodiments, the cap 16 has a larger diameter or cross-section than the removal rod 14.

As illustrated in FIG. 1, the removable medical device 10 can have an anchor portion 30. The anchor portion 30 can attach to the hub 12. In some embodiments, the anchor portion 30 attaches to the portion of the hub 12 opposite the valve portion 20. In some embodiments, the anchor portion 30 is attached to the same portion of the hub as the valve portion 20. The anchor portion 30 can include one or more anchors 31. The one or more anchors 31 can attach to the hub 12. In some embodiments, the one or more anchors 31 attach to the portion of the hub 12 opposite the valve portion 20. In some embodiments, the anchors 31 attach to the same portion of the hub as the valve portion 20. In some embodiments, the anchors 31 include an anchor arm 32. In some embodiments, the anchors 31 include a piercing member 34 on the end of the anchors 31 opposite the hub 12. The piercing member 34 can be configured to penetrate the tissue of the walls in the region in which the medical device 10 is deployed. In some embodiments, the anchors 31 include a pad 36 adjacent the piercing member 24 on the end of the anchors 31 opposite the hub 12. In some embodiments, the pad 36 can limit the depth to which the piercing members 34 can penetrate tissue.

In some embodiments, the valve portion 20 can be configured to transition between a compressed configuration and an expanded configuration. For example, the struts 24 can be configured to compress inwardly toward the rod 14 upon the application of a compressing force on the struts 24 and/or membrane portion 22. In some embodiments, the struts 24 are biased to the expanded configuration. In some embodiments, the struts 24 are shape-set to the expanded configuration. In some embodiments, the struts 24 can be constructed of Nitinol or some other suitable material.

In some embodiments, the anchoring portion 30 can be configured to transition between a compressed configuration and an expanded configuration. For example, the anchors 31 can be configured to bend inwardly and away from the hub 12 upon application of a compressing force on the anchors 31. In some embodiments, the anchors 31 are biased to the expanded configuration. In some embodiments, the anchors 31 are shape-set to the expanded configuration. In some embodiments, the anchors 31 can be constructed of Nitinol or some other suitable material.

Figure 2A:
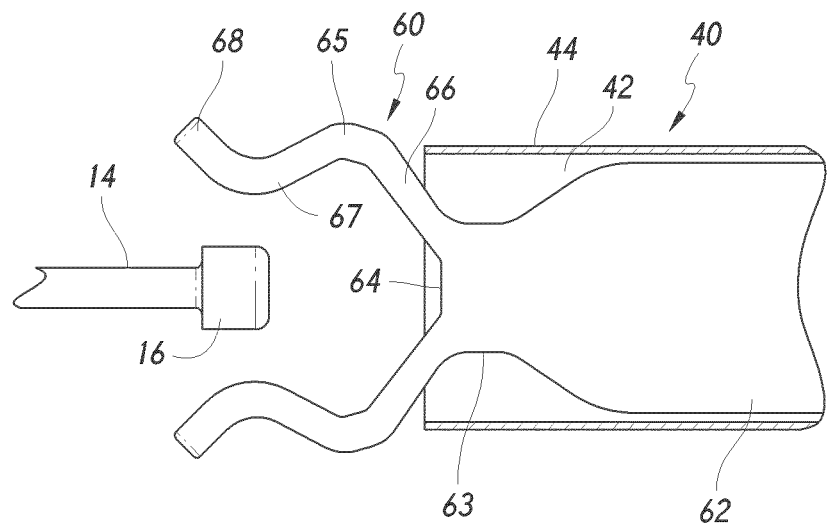
FIG. 2A is a view of a tool useful for repositioning or removing a medical device, which tool is shown in an opened configuration.
Figure 2B:
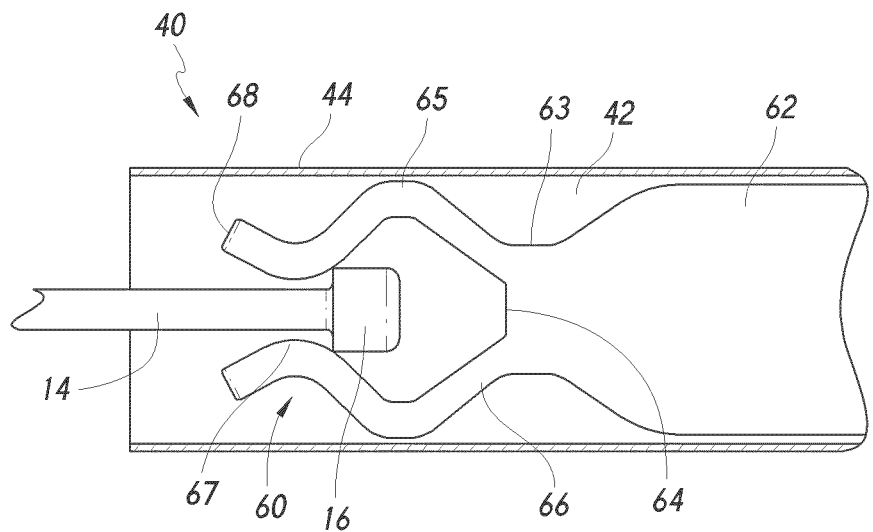
FIG. 2B is a view of the tool of FIG. 2A in a closed configuration.

FIGS. 2A and 2B illustrate an embodiment of an operative portion 60 of a tool that can be used for removing and/or repositioning a medical device 10. In some embodiments, the operative portion 60 can be configured to transition between an opened configuration (as illustrated in FIG. 2A) and a closed configuration (as illustrated in FIG. 2B). In some embodiments, the removal device 60 can include a proximal portion 62. In some embodiments, the proximal portion 62 can be hollow. In some embodiments, at least a portion of the proximal portion 62 is solid. In some embodiments, the proximal portion 62 can be constructed of a rigid, semi-rigid, or flexible material. In some embodiments, the proximal portion 62 can be constructed of the same material as the remainder of the operative portion 60 of the tool for removing and/or repositioning a medical device 10. In some configurations, the proximal portion 62 and the operative portion 60 can be integrally formed or monolithic in configuration.

In some embodiments, the operative portion 60 can include one or more engagement members 66. In some embodiments, the one or more engagement members 66 are attached to the distal end of the proximal portion 62. The one or more engagement members 66 can be configured to be moveable toward one another. In some embodiments, movement of the one or more engagement members 66 toward one another can transition the operative portion 60 to the closed configuration. In some embodiments, movement of the one or more engagement members 66 away from one another can transition the operative portion 60 to the opened configuration. In some embodiments, the one or more engagement members 66 can be biased to the opened configuration. In some embodiments, the operative portion 60 can include one or more indentations 63. In some embodiments, the indentations 63 can reduce the force required to transition the one or more engagement members 66 between the opened configuration and the closed configuration.

The one or more engagement members 66 can include an expanded portion 65 connected to the distal end of the proximal portion 62. In some embodiments, the expanded portion 65 extends outwardly from the proximal portion 62 with respect to a central axis of the operative portion 60 when the operative portion 60 is in the closed configuration. In some embodiments, the expanded portion 65 extends outwardly with respect to the central axis of the operative portion 60 from a connection point between the engagement members 66 and the proximal portion 62 when the operative portion 60 is in the opened or closed configuration. In some embodiments, the connection between the engagement members 66 and the proximal portion 62 defines a proximal backstop 64 (e.g., when the proximal portion 62 comprises a solid part). In some embodiments, the engagement members 66 have a grasping portion 67. In some embodiments, the grasping portion 67 can be attached to the distal end of the expanded portion 65. In some embodiments, the grasping portion 67 can extended inwardly with respect to the central axis of the operative portion 60 from the expanded portion 65.

In some embodiments, the operative portion 60 includes distal tips 68 on the ends of the engagement members 66. In some embodiments, the distal tips 68 of the engagement members can be connected to the distal ends of the grasping portions 67. In some embodiments, the distal tips 68 extend outwardly from the grasping portions 67 with respect to the central radius of the operative portion 60. In some embodiments, the distal tips 68 define atraumatic structures such that any body structure can be somewhat protected during contact between the distal tips 68 and the body structure. The distal tips 68 and/or other portions of the engagement members 66 can be configured to widen the body structure (e.g., a body lumen such as an airway) within which the engagement members 66 are transitioned to the opened configuration. For example, the engagement members 66 (or some portion thereof) can widen the body lumen in which a device 10 is implanted. In some embodiments, widening of the body lumen in which a device 10 is implanted can help to disengage the device 10 (or some portion thereof) from the walls of the body lumen (e.g., help to disengage the device 10 from surrounding hyperplastic portions of the body lumen).

Figure 2C:
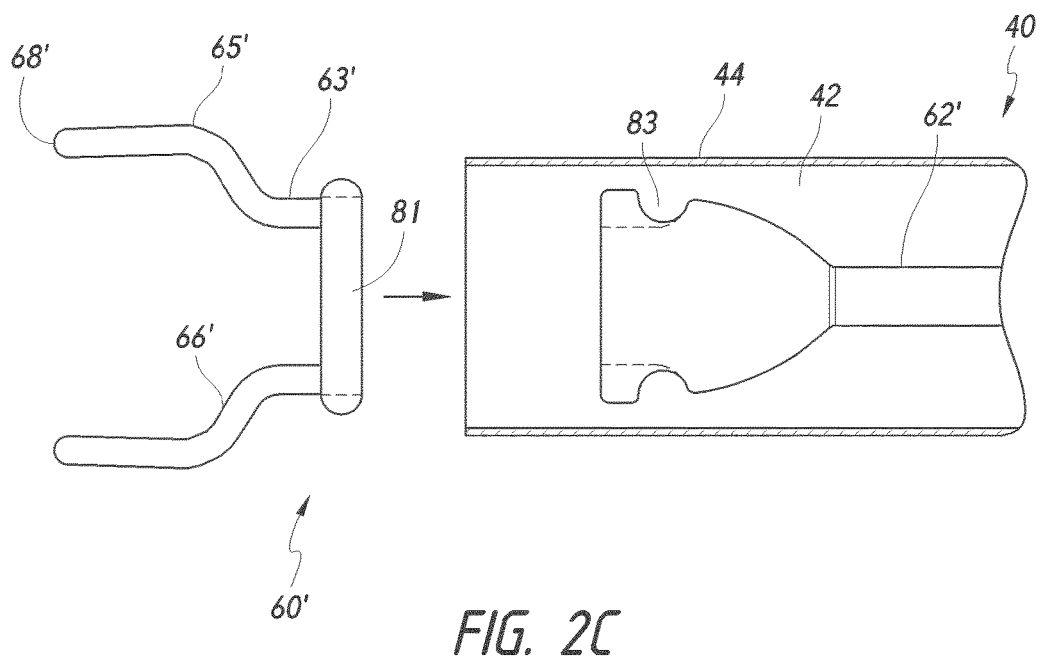
FIG. 2C is a view of another tool with a removable portion in the detached and opened configuration.
Figure 2D:
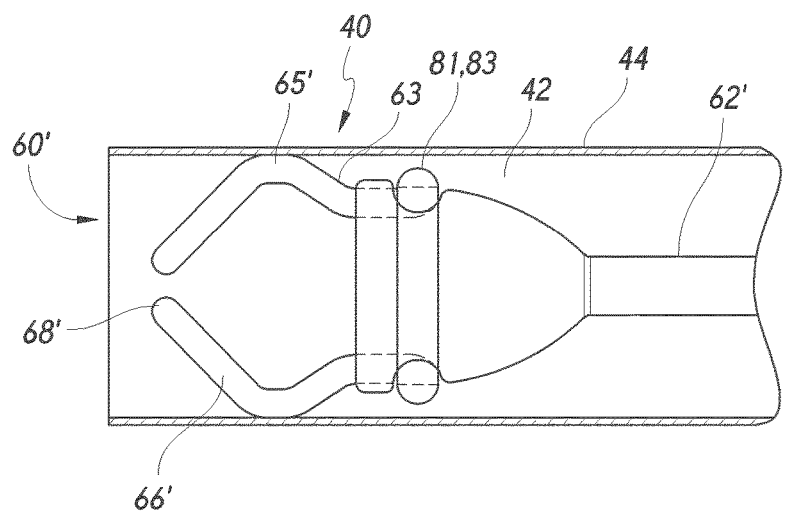
FIG. 2D is a view of the tool of FIG. 2C in the attached and closed configuration.

FIGS. 2C and 2D illustrate an embodiment of an operative portion 60' of a tool that can be used for removing and/or repositioning a foreign body (e.g. a medical device). Some numerical references to components in FIGS. 2C and 2D are the same or similar to those previously described for the operative portion 60 described above except that prime (') has been added. It is to be understood that the components can be the same in function or are similar in function to previously-described components. The operative portion 60' of FIGS. 2C and 2D shows certain variations to the operative portion 60 of FIGS. 2A and 2B.

In some embodiments, the engagement portions 66' are removable from the proximal portion 62'. In some embodiments, the proximal portion 62' includes a groove 83. The proximal ends of the engagement portions 66' can be configured to connect with a band 81. The band 81 can be constructed of nitinol or any other suitable material. In some embodiments, the band 81 can be configured to removably engage with the groove 83. In some embodiments, the engagement members 66' can be constructed of nitinol or any other suitable material. In some embodiments, the engagement member 66' and the band 81 form a unitary part. In some embodiments, the engagement members 66' can be biased in the opened configuration.

Figure 3A:
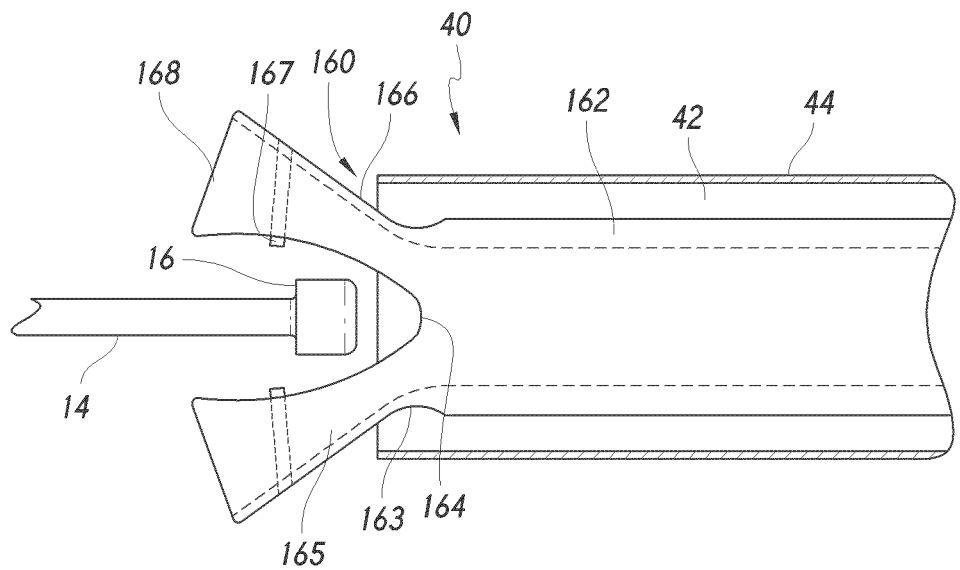
FIG. 3A is a view of another tool in an opened configuration.

FIGS. 3A-4B illustrate an embodiment of an operative portion 160 of a tool that can be used for removing and/or repositioning a medical device 10. In some embodiments, the operative portion 160 can be configured to transition between an opened configuration (as illustrated in FIG. 3A) and a closed configuration (as illustrated in FIG. 3B). In some embodiments, the operative portion 160 can include a proximal portion 162. In some embodiments, the proximal portion 162 is hollow. In some embodiments, at least a portion of the proximal portion 162 is solid. In some embodiments, the proximal portion 162 can be constructed of a rigid, semi-rigid, or flexible material. In some embodiments, the proximal portion 162 can be constructed of the same material as the remainder of the operative portion 160 of the tool for removing and/or repositioning a medical device 10. In some embodiments, the operative portion 160 is formed from a tubular piece of material (e.g. Nitinol or some other suitable material). In some configurations, the proximal portion 162 and the operative portion 160 can be monolithic in configuration or integrally formed.

In some embodiments, the operative portion 160 includes one or more engagement members 166. The engagement members 166 can extend distally from the proximal portion 162. In some embodiments, the engagement members 166 include expanded portions 165. The expanded portions 165 can extend outwardly away from a central axis of the operative portion 160 when the operative portion 160 is in the opened or closed configuration. In some embodiments, the expanded portion 165 can extend in the distal direction substantially parallel to the walls of the proximal portion 162 when the operative portion 160 is in the closed configuration. In some embodiments, the expanded portion 165 can extend inwardly toward the central axis of the operative portion 160 when the operative portion 160 is in the closed configuration.

In some embodiments, the engagement members 166 can include one or more grasping portions 167. In some embodiments, the grasping portions 167 extend inwardly from the engagement members 166 toward the central axis of the operative portion 160. In some embodiments, the grasping portions 167 extend inwardly as well as in the proximal direction. In some embodiments, the grasping portions 167 extend inwardly as well as in the distal direction. In some embodiments, the grasping portions 167 are formed by making two or more cuts in the engagement members 166 and bending the cut portion of the engagement members 166 inwardly toward the central axis of the operative portion 160. In some embodiments, the grasping portions 167 are formed by making at least two substantially parallel cuts in the engagement members 166 and flexing the cut portion inwardly toward the central axis of the operative portion 160. In some embodiments, the grasping portions 167 are formed by making at least two cuts in the engagement members 166, each cut extending to a distal end 168 of the engagement members 166 such that the cut portion can be folded down toward the central axis of the operative portion 160 to form the grasping portions 167. In some embodiments, the radial length of each of the grasping portions 167 is less than half the length of the inner diameter of the engagement members 166. In some embodiments, the radial length (e.g., the length substantially perpendicular to the central axis of the operative portion 160) of each of the grasping portions 167 is less than half the distance between the inner walls of the engagement members 166. In some embodiments, the total radial length of the one or more grasping portions 167 is less than the distance between the inner walls of the engagement members 166.

Figure 3B:
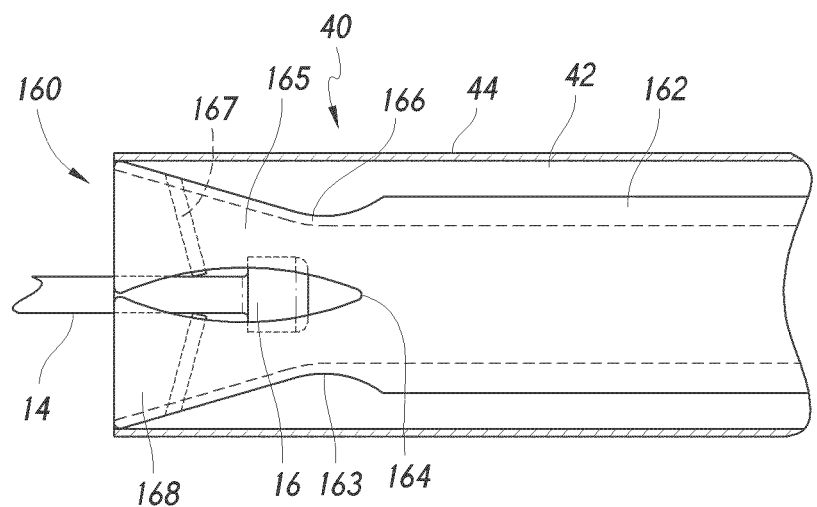
FIG. 3B is a view of the tool of FIG. 3A in a closed configuration.

In some embodiments, the connection between the engagement members 166 and the proximal portion 162 can form a back portion 164. In some embodiments, the distal ends 168 of the engagement members 166 can come into contact with each other when the operative portion 160 is in a closed configuration. In some embodiments, the distal ends 168 of the engagement members 166 can have a semi-circular or curved shape (e.g. when viewed along the central axis of the operative portion 160). In some embodiments, the distal ends 168 of the engagement members 166 can be flat (e.g. when viewed along the central axis of the operative portion 160). In some embodiments, the space formed between the back portion 164 and engagement members 166 can form substantially "tear drop" shaped space when the operative portion 160 is in a closed configuration, as illustrated in FIG. 3B.

In some embodiments, the operative portion 160 can include one or more indentations 163. In some embodiments, the indentations 163 can be located near the proximal ends of the engagement members 166. In some embodiments, a thickness of the indentations 163 in a direction substantially perpendicular to the central axis of the operative portion 160 can be less than a thickness of the operative portion 160 distal and/or proximal of the indentations 163 in the direction substantially perpendicular to the central axis of the operative portion 160. The indentations 163 can decrease the force required to transition the operative portion 160 between the opened configuration and the closed configuration.

In some configurations, a method of removing and/or repositioning a medical device 10 from an airway or other body lumen can include the step of grasping the medical device 10 using the operative portion 160 of a tool for removing and/or repositioning a medical device 10. For example, with reference to FIGS. 3A-4B, the operative portion 160 of the tool for removing and/or repositioning a medical device 10 can be include a sleeve 40. In some embodiments, the sleeve 40 can be a catheter, the working channel of an endoscope, or any other suitable lumen, conduit, or tube. In some embodiments, the sleeve 40 includes a sleeve lumen 42. In some embodiments, the sleeve 40 includes sleeve walls 44. In some embodiments, the total radial length of the one or more grasping portion 167, the diameter of the rod 14 of the medical device 10, and the wall thicknesses at the distal end of the two or more engagement member 166 can be less the inner diameter of the sleeve 40.

In some embodiments, the sleeve 40 can be moved in the distal and/or proximal directions with respect to the operative portion 160. As described above, the engagement members 166 of the operative portion 160 can be biased to the opened configuration. In some configurations, the engagement members 166 can be configured to transition to the closed configuration when the sleeve 40 moves over the distal ends 168 of the engagement members 166, as illustrated, for example, in FIGS. 3B and 4B. In some embodiments, the engagement members 166 can be configured to transition to the opened configuration when the distal end of the sleeve 40 is moved from beyond the distal ends 168 of the engagement members 166 to proximal of the engagement members 166. As explained above with reference to FIGS. 2A-2B, the engagement member 166 can be configured to expand the body lumen in which the engagement members 166 are transitioned to the opened configuration. In some embodiments, expansion of the body lumen by the engagement members 166 (or some portion thereof) can help to disengage a target device 10 (e.g., a device to be removed) from adjacent portions of the body lumen (e.g., hyperplastic portions of the body lumen).

In some embodiments, the tool for removing and/or repositioning medical devices can include a stabilizing portion proximal of the proximal portion 162 of the operative portion 160. The stabilizing portion can allow the operative portion 160 to be held in place within the body of the patient while the sleeve 40 is moved in the proximal and/or distal directions with respect to the operative portion 160. In some embodiments, the stabilizing portion can be a wire extending in the proximal direction from the proximal end of the proximal portion 162. In some embodiments, the stabilizing portion can be a tube extending in the proximal direction from the proximal end of the proximal portion 162. In some embodiments, the proximal portion 162 can be a unitary part with the stabilizing portion. In some embodiments, the stabilizing portion can allow the user of the operative portion 160 to move the operative portion 160 in the distal and/or proximal directions with respect to the sleeve 40.

Figure 4A:
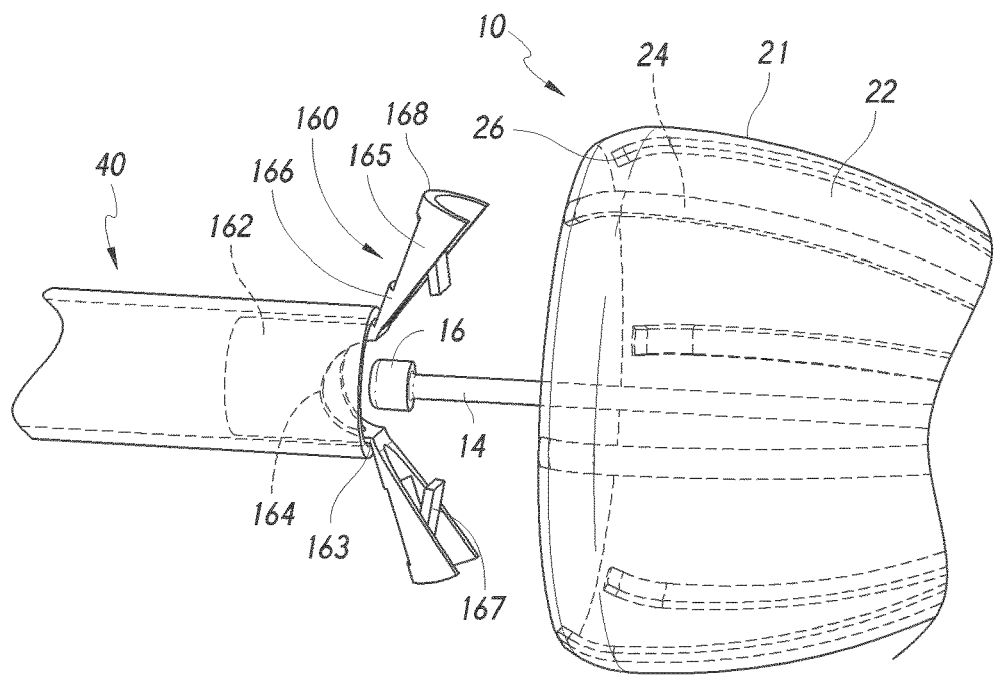
FIG. 4A is a perspective view of the tool of FIG. 3A in an opened configuration.
Figure 4B:
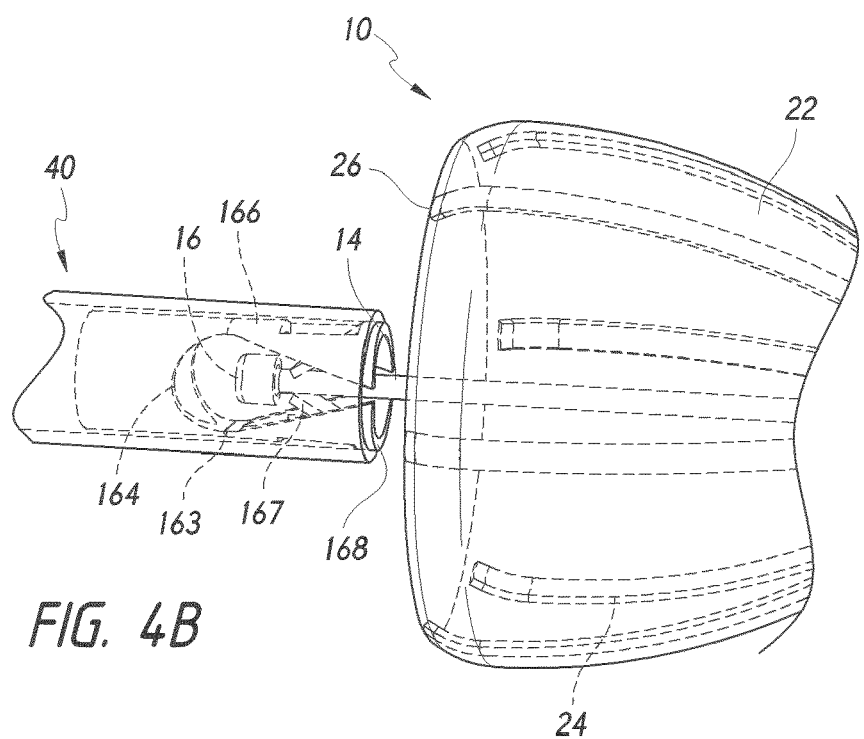
FIG. 4B is a perspective view of the tool of FIG. 3A in a closed configuration.

With reference to FIGS. 3A and 4A, the operative portion 160 can be positioned near the cap 16 on the end of the central rod 14 of a medical device 10. In some embodiments, the sleeve 40 can be withdrawn from the operative portion 160 in the proximal direction. The engagement members 166 then can transition to the opened configuration. The operative portion 160 then can be moved toward the central rod 14 of the medical device 10 until the central rod 14 and/or cap 16 are positioned within the engagement members 166 such that the cap 16 is located proximal to the grasping portions 167, as illustrated, for example, in FIGS. 3A and 4A. The sleeve 40 then can be moved distally with respect to the operative portion 160 so that the engagement members 166 transition toward the closed configuration, as illustrated, for example, in FIGS. 3B and 4B.

In some embodiments, the grasping portions 167 can secure the cap 16 within the operative portion 160 when the engagement members 166 are transitioned to the closed configuration while the cap 16 is located proximal to the grasping portions 167. The operative portion 160 then can be used to pull the medical device 10 in the proximal direction. In some embodiments, the operative portion 160 can be configured to push the medical device 10 in the distal direction when the cap 16 is secured within the operative portion 160.

Figure 3C:
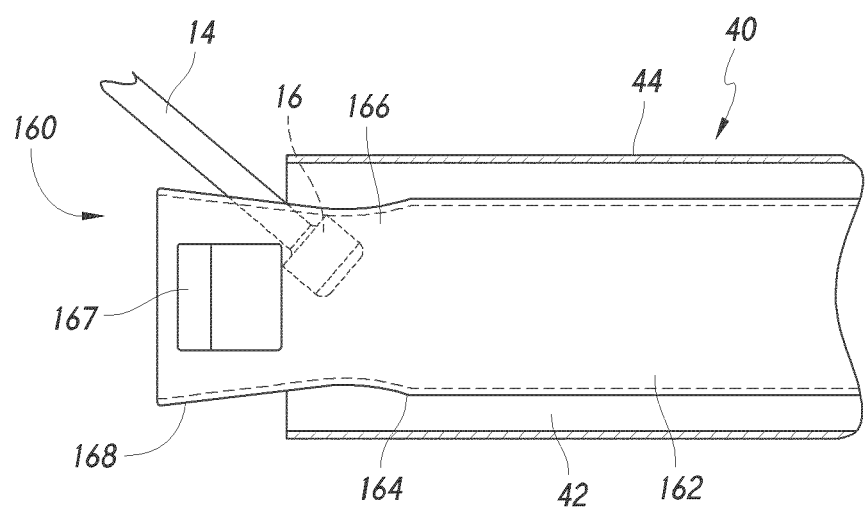
FIG. 3C is a view of the tool of FIG. 3A in a closed configuration grabbing an off-axis device.

In some embodiments, the "tear drop" shaped space formed by the back portion 164 and engagement members 166 can make it easier for the user of the operative portion 160 to grasp a cap 16 on the end of a central rod 14 in situations where the central axes of the medical device 10 and operative portion 160 are not aligned with one another, as illustrated in FIG. 3C. In such a situation, the operative portion 160 can, in some embodiments, be used to pull the medical device 10 in the proximal direction and/or push the medical device 10 in the distal direction.

Although a method of grasping a medical device 10 has been described in the context of the embodiment of the operative portion 160 illustrated in FIGS. 3A-4B, the same general method can be performed using the embodiment of the operative portion 60 found in FIGS. 2A and 2B.

Figure 5:
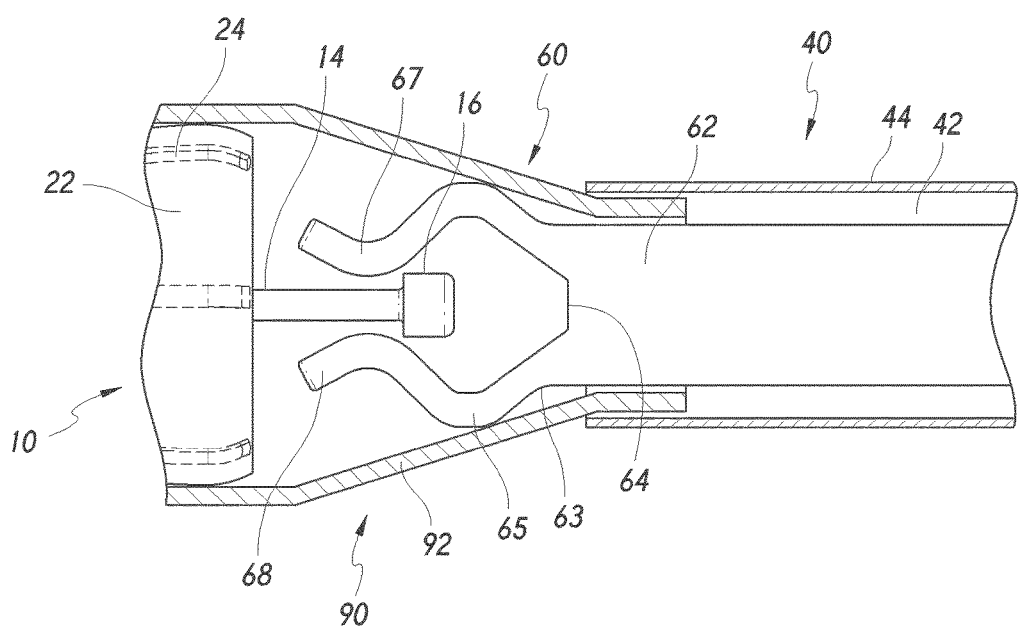
FIG. 5 is a view of a tool engaged with a valve loading tool.

FIG. 5 illustrates a method of using the operative portion 60 of a tool for removing and/or repositioning medical devices 10 to pull a medical device 10 through the interior of a compressing device 90 into the interior of the sleeve 40. In some embodiments, the compressing device 90 can include a tapered portion 92. The tapered portion 92 can be constructed from a flexible or semi-flexible material configured to stretch and/or bend when in contact with the medical device 10 and/or with the walls of the body lumen in which the medical device 10 is implanted. In some embodiments, the tapered portion 92 is constructed from a rigid or semi-rigid material. The operative portion 60 can be used to grasp the cap 16 on the end of the central rod 14 and pull the device 10 toward the sleeve 40. In some embodiments, the tapered portion 92 can help transition the struts 24 and/or anchors 31 of the device 10 from the expanded configuration to the compressed configuration as the device 10 is pulled toward the sleeve 40. Examples of tapering devices can be found in U.S. Pat. Nos. 8,043,301 and 8,136,230, which are hereby incorporated by reference herein in their entireties.

Figure 6:
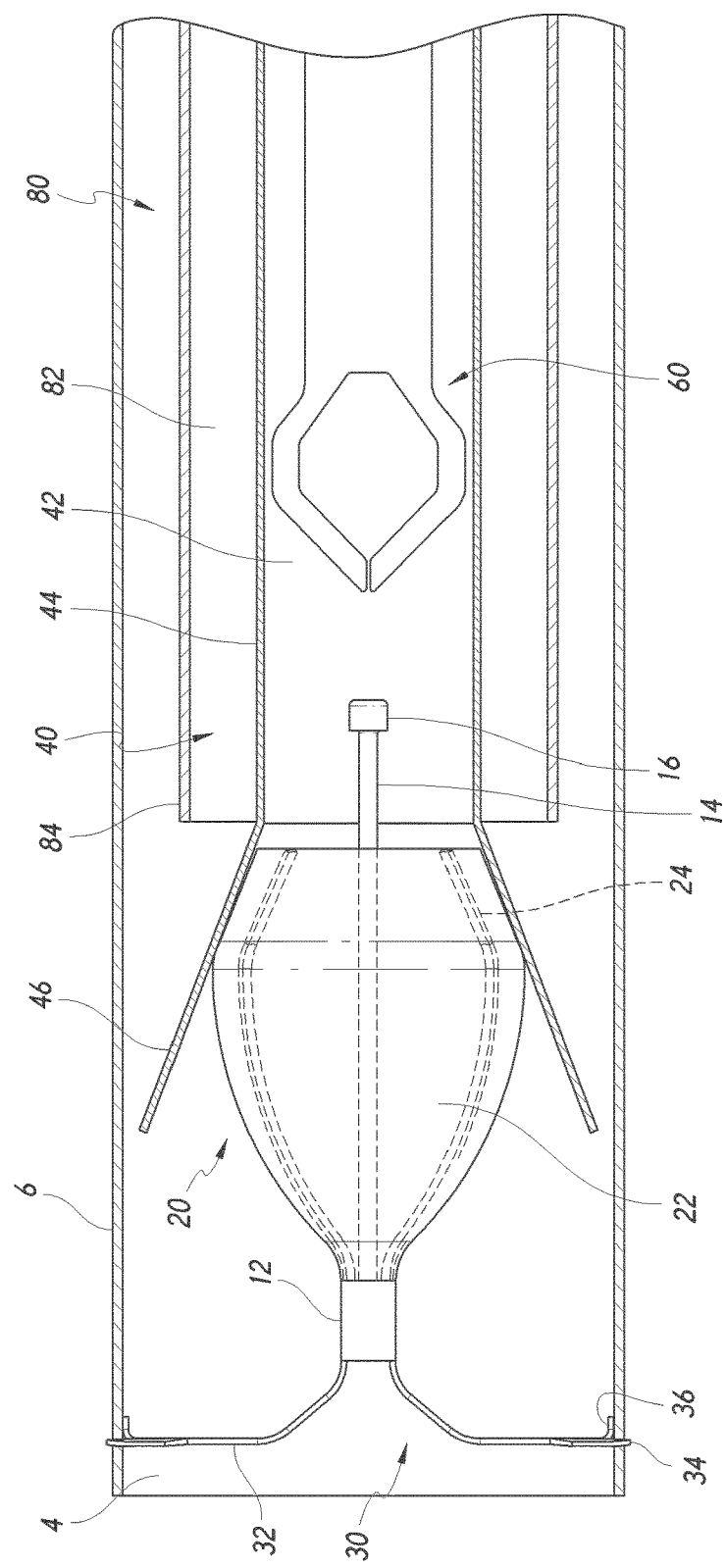
FIG. 6 is a view of a tool having a flared distal end.
Figure 7:
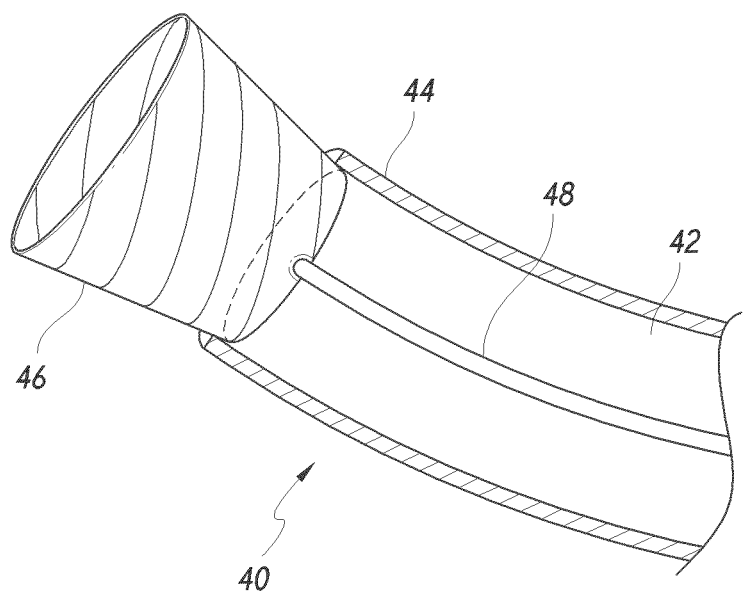
FIG. 7 is a view of a tool having a spiral flared distal end.

In some embodiments, a tool for removing and/or repositioning medical devices 10 can include a compressing portion 46. In some embodiments, the compressing portion 46 is conical or frustoconical in shape, as illustrated in FIGS. 6 and 7. In some embodiments, the compressing portion 46 is fluted (e.g., the radius of the compressing portion 46 increases at a decreasing rate toward the distal end of the compressing portion 46) or trumpeted (e.g., the radius of the compressing portion 46 increases at an increasing rate toward the distal end of the compressing portion 46) in shape. In some embodiments, the compressing portion 46 can have fluted portions, trumpeted portions, conical portions, frustoconical portions, or any combination thereof. In some embodiments, the compressing portion 46 is attached to the distal end of the sleeve 40. The sleeve 40 can be delivered to site of the medical device 10 via a working channel 82 of a deliver device 80 (e.g., a working channel of a catheter, bronchoscope, endoscope, or other delivery device). In some embodiments, the compressing portion 46 is attached to a rod or wire 48. In embodiments, the compressing portion 46 is attached to the wire 48 via welding, adhesives, soldering, magnets, or some other suitable method of affixing the wire 48 to the compressing portion 46. In some embodiments, the compressing portion 46 can be moved in the distal and/or proximal direction with respect to the sleeve 40. In some embodiments, the compressing portion 46 can be moved in the distal and/or proximal direction with respect to the operative portion 60. In some embodiments, the compressing portion 46 is fixed to the sleeve 40. In some embodiments, the compressing portion 46 is a unitary part with the sleeve 40.

The compressing portion 46 can be constructed of a rigid, semi-rigid, or flexible material. In some embodiments, the compressing portion 46 is constructed of the same material as the sleeve 40 and/or the operative portion 60. In some embodiments, the compressing portion 46 is constructed of Nitinol or some other shape memory material. The compressing portion 46 can be constructed of a series of overlapping spiraled panels, as illustrated in FIG. 7. In some embodiments, the compressing portion 46 can be constructed of a single piece of material. In some embodiments, the compressing portion 46 can have a window cut into to allow for visualization through the compressing portion 46.

In some embodiments, the compressing portion 46 can be configured to transition between a compressed configuration and an expanded configuration. In some embodiments, the compressing portion 46 is configured to transition from the compressed configuration to the expanded configuration (e.g., as illustrated in FIG. 6) upon withdrawal of the delivery device 80 from the compressing portion 46. In some embodiments, the compressing portion 46 can be biased to the expanded configuration, as illustrated in FIGS. 6 and 7. For example, the compressing portion 46 can be biased to the expanded configuration such that, as the distal end 84 of the delivery device 80 is withdrawn from the compressing portion 46, the compressing portion 46 expands within the airway 4 or other body lumen. In some embodiments, compressing portion 46 can be configured to transition to the compressed configuration when the compressing portion 46 is positioned within the sleeve 40 or some other lumen or conduit (e.g. the working channel of an endoscope). In some configurations, the compressing portion 46 can be configured to at least partially retract into the sleeve 40. In some embodiments, the compressing portion 46 can be configured to apply expansive force upon and expand the tissue 6 of an airway 4 or other body lumen when the compressing portion 46 is in the expanded configuration.

Figure 8A:
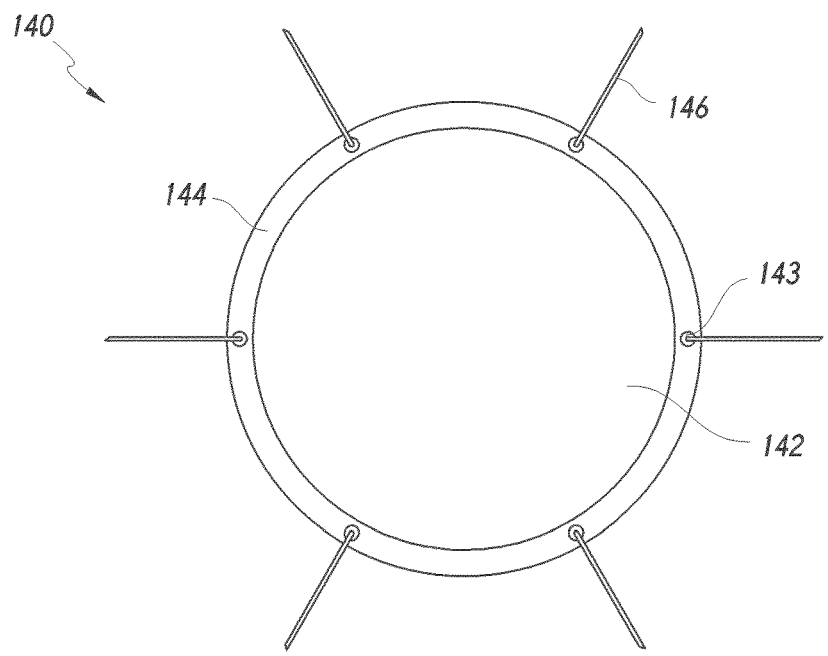
FIG. 8A is a distal end view of a multi-lumen tool having a plurality of guide-wires.
Figure 8B:
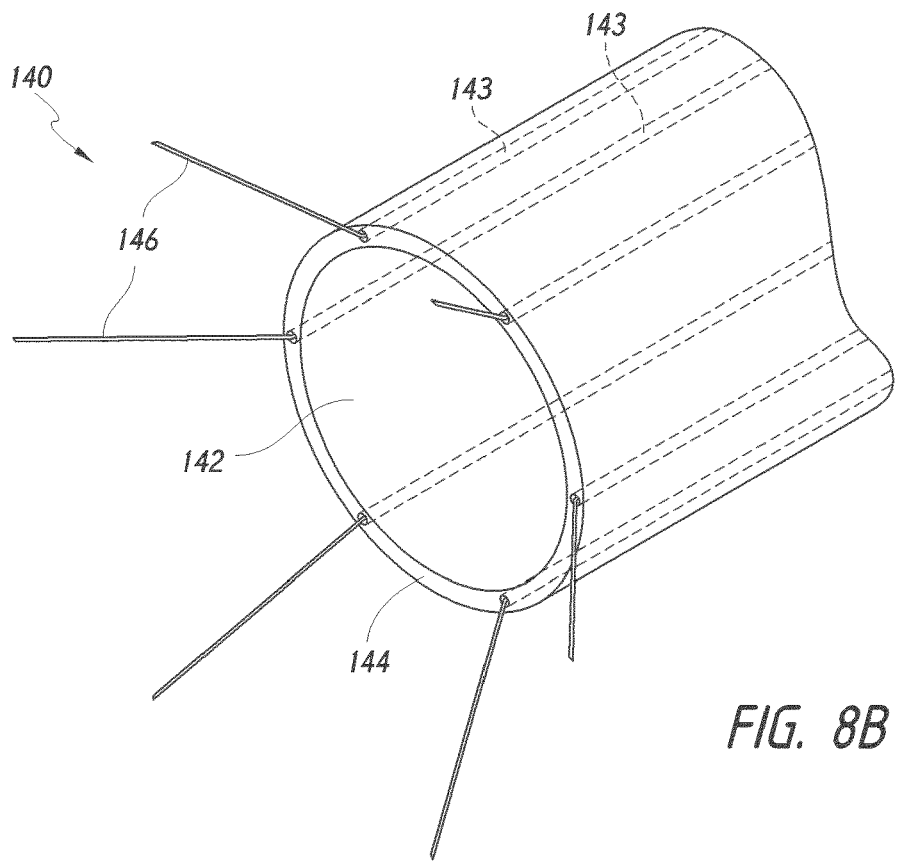
FIG. 8B is a perspective view of the multi-lumen tool of FIG. 8A.
Figure 8C:
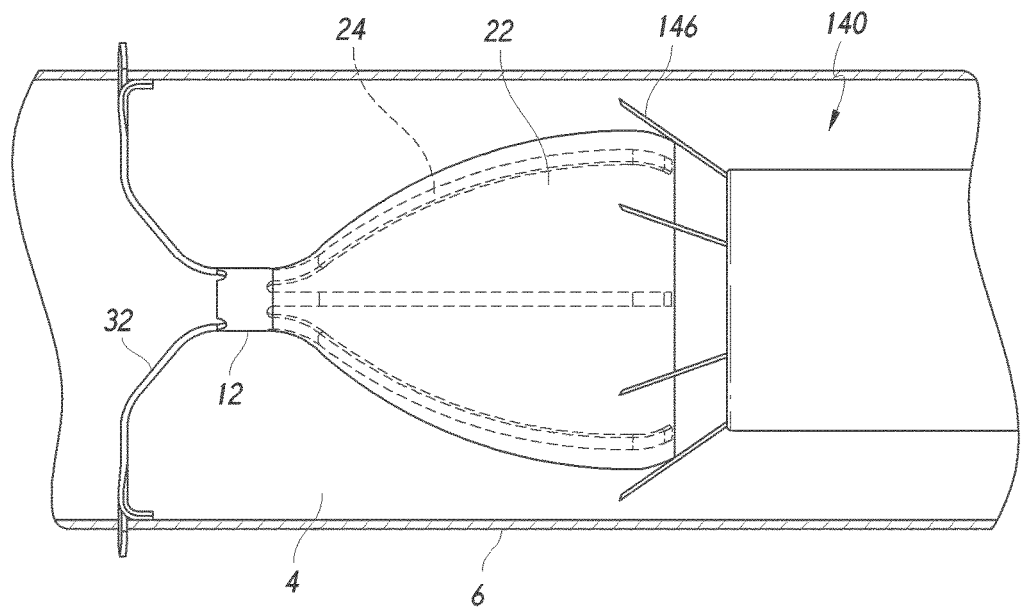
FIG. 8C is a view of the multi-lumen tool of FIG. 8A within an airway or other body lumen.

In some embodiments, the tool for removing and/or repositioning medical devices can include a plurality of compression wires 146, as illustrated in FIGS. 8A and 8B. The compression wires 146 can be housed in one or more secondary conduits 143 within a sleeve 140. In some embodiments, the number of compression wires 146 and/or corresponding secondary conduits 143 used can match the number of struts 24 on the medical device 10 to be removed/repositioned. In some embodiments, the number of wires 146 and/or corresponding secondary conduits 143 used can be fewer than the number of struts 24. In some embodiments, the number of wires 146 and/or corresponding secondary conduits 143 can be more than the number of struts 24. In some embodiments, the compression wires 146 can be configured to transition from a compressed configuration to an expanded configuration upon extension of the wires 146 from the secondary conduits 143. In some embodiments, the compression wires 146 can be configured to transition from the expanded configuration to the closed configuration upon the return of the wires 146 into the secondary conduits 143. In some embodiments, the compression wires 146 can be constructed of Nitinol or some other suitable material. In some embodiments, the compression wires 146 can include a stabilizing member. In some embodiments, the stabilizing member can have a circular or semi-circular shape and can extend between each of the individual compression wires 146 (e.g. on or more rings of material which connect one or more of the individual compression wires 146 to each other). In some embodiments, the stabilizing member can limit movement of the compression wires 146 in the tangential direction (e.g., tangential with respect to the central axis of the sleeve 140) toward or away from each other. In some configurations, the stabilizing member can form a loop that somewhat controls a diameter to which the wires can expand.

Figure 8D:
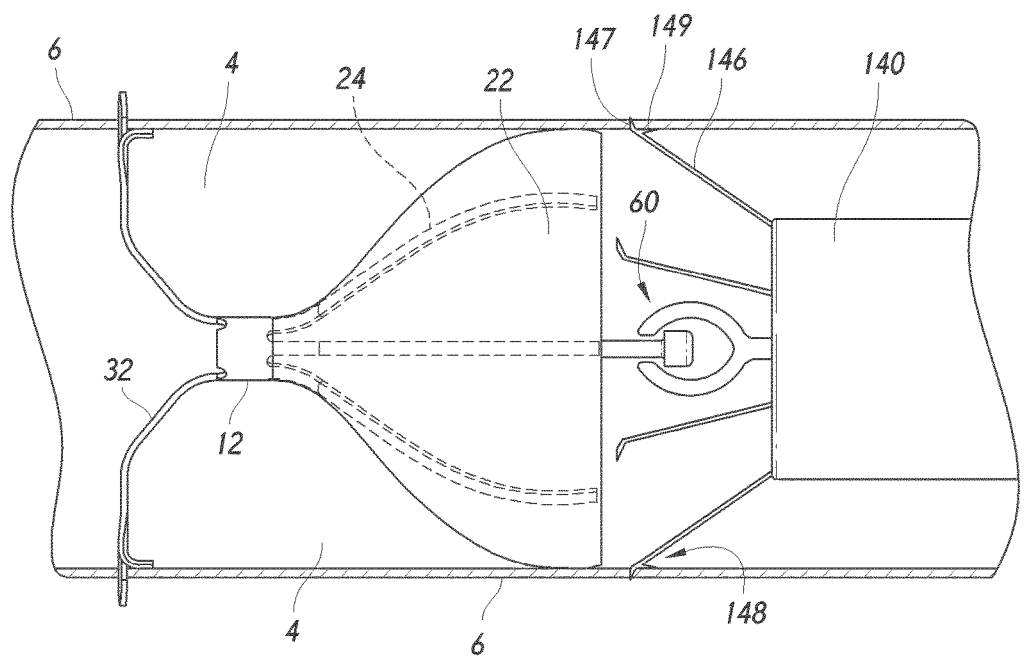
FIG. 8D is a view of an embodiment of the tool of FIG. 8A having distal anchors on the guide-wires.

In some embodiments, the wires 146 can include anchoring portions. In some configurations, the anchoring portions can be formed on the distal ends of the wires 146, as illustrated in FIG. 8D. In some embodiments, the anchoring portions of the wires 146 can include a piercing member 147. In some embodiments, the piercing members 147 can be configured to penetrate the tissue 6 of an airway 4 or other body lumen when the wires 146 are in the expanded configuration. In some embodiments, the anchoring points of the wires 146 can include pads 149. The pads 149 can be configured to limit the depth to which the piercing members 147 can penetrate the tissue 6.

The wires can have any desired cross-section. The cross-section can be substantially uniform along the length of the wire or the cross-section can vary. In some embodiments, a tool for removing and/or repositioning a medical device 10 can include a plurality of flat compression wires 246. The flat wires 246 can be housed within a plurality of secondary conduits 243 within a sleeve 240. The flat wires 246 can be configured to transition from a compressed configuration to an expanded configuration upon extension of the flat wires 246 from the secondary conduits 243. In some embodiments, the flat wires 246 can be configured to transition from the expanded configuration to the compressed configuration upon the return of the flat wires 246 into the secondary conduits 243.

A method of compressing a medical device 10 into a device to remove and/or reposition a medical device 10 can include the step of grasping the cap 16 on the end of a rod 14 of the medical device 10, as described above. In some embodiments, the method can include transitioning the compressing portion 46 to the expanded configuration, as illustrated in FIG. 6. The operative portion 60 then can be used to pull the medical device 10 toward the compressing portion 46 or to hold the medical device 10 stable while the compressing portion 46 is advanced toward the medical device 10. In some embodiments, the operative portion 60 can be used to hold the medical device 10 in place as the compressing portion 46 is moved toward the medical device. As the medical device 10 is received into the compressing portion 46, the flared shape of the compressing portion 46 can cause the medical device 10 to transition to a compressed configuration. For example, the struts 24 of the medical device 10 can come into contact with the compressing portion 46 and can be urged toward the central rod 14 of the medical device 10. Compression of the struts 24 can cause the valve portion 20 of the medical device 10 transition to the compressed configuration. In some embodiments, the anchors 31 of the medical device 10 can be configured such that the piercing members 34 of the anchors 31 disengage from the tissue 6 as a result of the bending of the anchors 31 when the medical device 10 is pulled in the proximal direction.

In some embodiments, the operative portion 60 can continue to pull the medical device 10 toward the sleeve 40 such that the anchors 31 are brought into contact with the compressing portion 46. In some embodiments, the operative portion 60 can continue to hold the medical device 10 stable while the compressing portion 46 is advanced further toward the medical device 10. In some embodiments, the compressing portion 46 is configured to compress the anchors 31 to a compressed position as the anchors 31 travel through the compressing portion 46 toward the sleeve 40. In some embodiments, the entire medical device 10 can be transitioned into the sleeve 40 prior to the medical device 10 being removed and/or repositioned. In some embodiments, at least or only a portion of the medical device 10 can be transitioned into the sleeve 40. In some embodiments, the medical device 10 is not transitioned into the sleeve 40 as the medical device 10 is removed and/or repositioned. In some embodiments, the anchors 31 can be captured and/or covered by the tool such that, as the captured device 10 is moved within the body, the tool can reduce the likelihood that the anchors 31 or other portions of the medical device 10 could damage tissue within the body of the patient (e.g., the vocal chords, airways, trachea, or other body parts).

In some embodiments, the tool for repositioning and/or removing medical devices 10 can be moved within the body after the medical device 10 is removed from a first position. In some embodiments, the tool can be used to move the medical device 10 to a second location within the body. In such embodiments, the operative portion 60, compressing portion 46 and/or sleeve 40 can be moved to the second location in the body. In some embodiments, the sleeve 40 and/or the compressing portion 46 can include visual and/or radiopaque markings. The markings can be visualized using a camera within the delivery device, fluoroscopy, and/or any other visualization known by those skilled in the art. The markings can provide visual and/or fluoroscopic verification of the position of the tool and/or the position of the compressed medical device 10 within the tool. In some embodiments, a user of the tool can position the tool in the second location using the markings as a guide. The markings can include one or more colored bands, pigmented bands, metallic bands, translucent portions, and/or any other appropriate means or structure for allowing the user to visualize the location of the tool and/or the medical device 10. In some embodiments, the markings are located on the distal end of the sleeve 40 and/or the compressing portion 46. In some embodiments, the markings identify the location of a specific portion (e.g., the hub, proximal end of the struts, distal end of the anchors, etc.) of the medical device 10 within the sleeve 40.

Once positioned in the second location, the sleeve 40 and/or compressing portion 46 of the device can be withdrawn from (e.g. moved proximally with respect to) the operative portion 60. In some embodiments, as the sleeve 40 and/or compressing portions 46 are withdrawn from the operative portion 60 and/or medical device 10, the medical device 10 is configured to transition to an expanded configuration at the second location. In some embodiments, withdrawal of the sleeve 40 from the operative portion 60 can allow the engagement members 66 to transition to the opened configuration and can allow the grasping portions 67 to disengage from the medical device 10. In this manner, a medical device 10 can be deployed in a second location within the body.

Figure 8E:
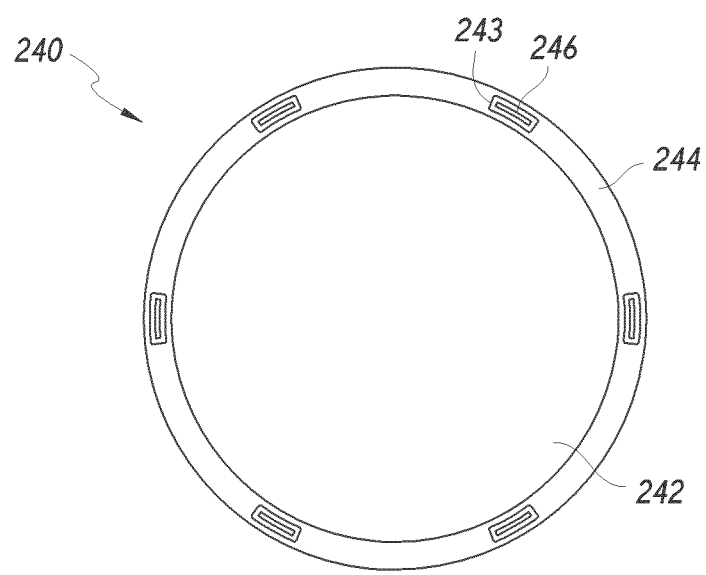
FIG. 8E is a distal end view of an embodiment of the tool of FIG. 8A having flat guide-wires.

Although the method of compressing and removing/repositioning a medical device 10 has been described with respect to the embodiment of the device illustrated in FIG. 6, the method can be similarly implemented using the embodiments of the device found in FIGS. 7-8E. For example, the compression wires 146 can be used to compress the valve portion 20 of the medical device 10 as the operative portion 60 pulls the medical device toward the sleeve 146. In some embodiments, the compression wires 146 can engage with the membrane portions 22 between the struts 24. In some embodiments, the compression wires 146 can penetrate built up tissue (e.g., hyperplasia) surrounding the valve portion 20 and can help remove the valve portion 20 of the medical device 10 from the walls of an airway 4 or other body lumen. In some embodiments, the anchor portions on the ends of the compression wires 146 can help hold the compression wires 146 in place as the valve portion 20 is compressed and can help reduce deflection of the compression wires 146 as the medical device 10 is pulled toward the sleeve 140. In some embodiments, the anchor portions on the ends of the compression wires 146 can be configured to release from the tissue 6 of the airway 4 when the compression wires 146 are pushed in the distal direction. In some embodiments, the anchor portions on the ends of the compression wires 146 can be configured to release from the tissue 6 of the airway 4 when the compression wires 146 are pulled in the proximal direction. In some embodiments, using flat compression wires 246 can help reduce the likelihood that the wires 246 will rotate with respect to the central axis of the operative portion 60, 160 and/or the central axes of the respective secondary conduits 243 as the medical device 10 is pulled toward the sleeve 240. In some embodiments, contact between the distal end of the sleeve 40, 140, 240 and the anchors 31 of the medical device 10 can cause the anchors 31 to transition to a compressed configuration.

Figure 9:
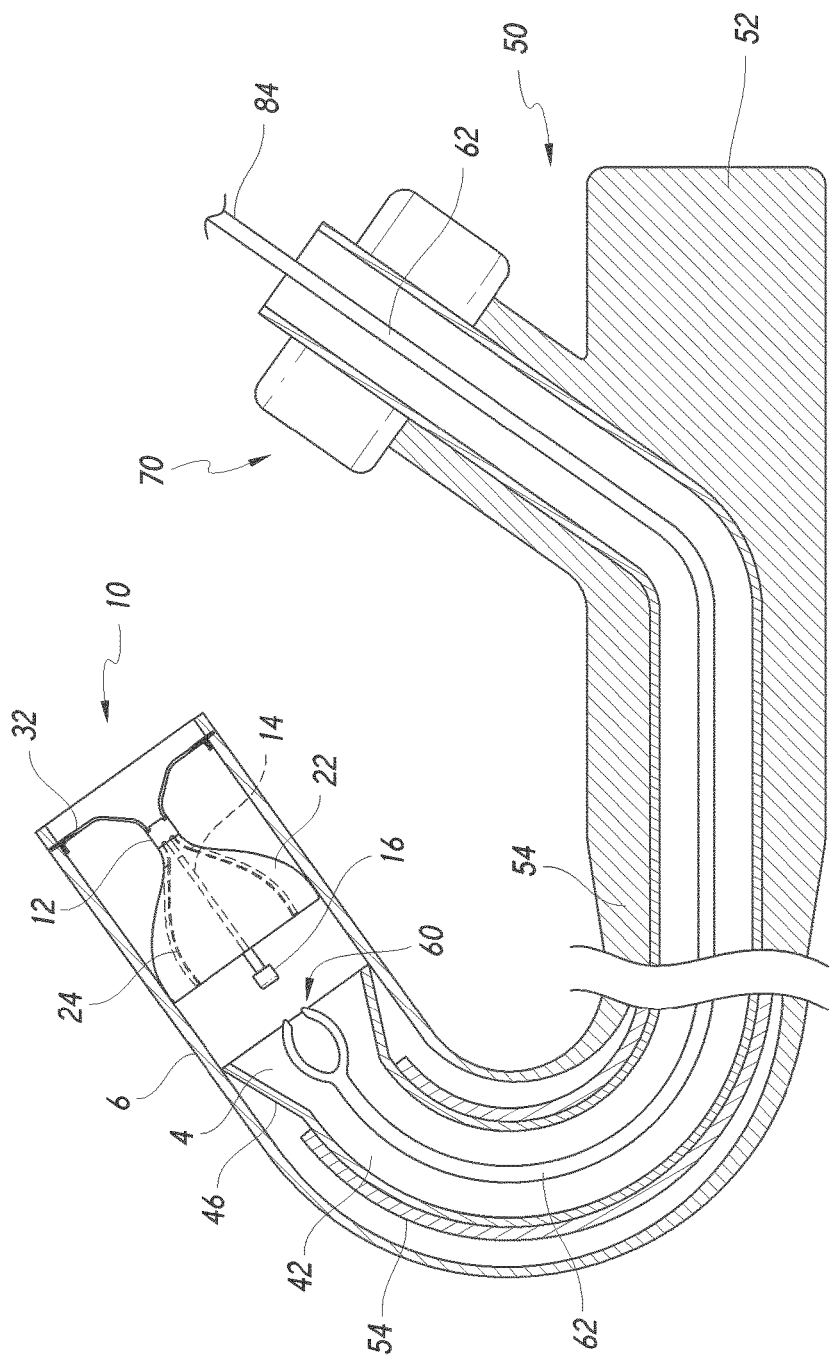
FIG. 9 is a view of a tool deployed within an airway or other body lumen via a working channel within an endoscope.

FIG. 9 illustrates an embodiment of the tool for removing and/or repositioning medical devices configured for use in an endoscope 50 or other delivery device. In some embodiments, the tool can be positioned within a working channel 54 of the endoscope 50. In some embodiments, the endoscope 50 or other delivery device can be used to navigate the tool through the patient's body to the site of a target medical device 10. The endoscope 50 can be guided from outside of the patient's body into an airway 4 of other body lumen. In some embodiments, a lock 70 can be used to hold portions (e.g., the operative portion 60, sleeve 40, and/or compressing portion 46) of the tool static with respect to the patient's body, the endoscope 50, and/or the other portions of the tool. In some embodiments, the lock 70 can be partially or completely released to allow for controlled movement of the portions of the tool with respect to one another (e.g., moving the sleeve in the distal and/or proximal direction with respect to the operative portion 60). The endoscope 50 can include a handle portion 52. In some embodiments, the handle portion 52 includes one or more controls or other user inputs (e.g., light controls, articulation controls, a vacuum control).

FIGS. 10A-10E illustrate an embodiment of a tool for repositioning and/or removing a medical device. The tool can include a capture portion 340. The capture portion 340 can include a body portion 342 with a proximal end 345. The proximal end 345 of the capture portion 340 can be configured to removably connect with the distal end of an endoscope 50 or other delivery device via the use of an adhesive, friction fitting, threading, magnets, or any other suitable method of adhering. The capture portion 340 can include one or more compression members 346. The compression members 346 can include hinge portions 343 where the compression members 346 connect to the body portion 342 of the capture portion 340. In some embodiments, capture portion 340 can include a single compression member 346. In some embodiments, the compression member 346 can have a conical shape, a fluted shape, a trumpeted shape, or any combination thereof. In some embodiments, the compression member 346 can be constructed of a single piece of material. In some embodiments, the compression member 346 can be constructed of overlapping panels of material. In some embodiments, the compression member 346 can be constructed of a plurality of wires. In some embodiments, the compression member 346 can be constructed of a plurality of woven wires.

In some embodiments, the compression members 346 can be configured to transition between an expanded configuration (as illustrated in FIG. 10C) and a compressed configuration (as illustrated in FIG. 10B) by moving about the hinge portions 343. In some embodiments, the one or more compression members 346 can be fixed in the expanded configuration. In some embodiments, the compression members 346 can be biased to the compressed configuration. In some embodiments, the compression members 346 can be biased to the expanded configuration. In some embodiments, the compression members 346 can be constructed of Nitinol or some other suitable material. In some embodiments, the compression members 346 can be transitioned to the expanded configuration by rotating a central ring 347 of the capture portion 240. The central ring 347 can be configured to rotate about an axis of rotation normal to or otherwise off axis from the central axis of the capture portion 340. In some embodiments, rotation of the central ring 347 can exert force on the interior of the compression members 346 such that the compression members transition to the expanded configuration. For example, the central ring 347 can be elliptical in shape such that a major diameter of the central ring 347 causes the ring 347 to come into contact with the compression members 346 when the central ring 347 is rotated toward coaxial (with respect to the central axis of the capture portion 340) alignment with the capture portion 340.

In some embodiments, each of the compression members 346 can include one or more internal lumens in communication with one or more internal lumens in the body portion 342. The one or more internal lumens can house a plurality of actuating wires. The actuating wires can have a bent shape such that, as the wires are extended from the body portion 342 into the lumens of the compression members 346, the wires can exert a radially-outward force on the compression members 346. In some embodiments, such a radially-outward force can cause the compression members 346 to transition from the compressed configuration to the expanded configuration. In some embodiments, the one or more internal lumens can house a plurality of actuating rods. In some embodiments, the actuating rods are straight. The actuating rods can be configured to extend and retract from the internal lumens of the body portion 342 into and out of the internal lumens of the compression members 346. In some embodiments, where the compression members 346 are biased to the expanded configuration, insertion of the actuating rods into the internal lumens of the compression members 346 can cause the compression members 346 to transition from the expanded configuration to the compressed configuration.

In some embodiments, the capture portion 340 can include an operative portion 160. In some embodiments, the operative portion 160 of the capture portion 340 is the same as or similar in both function and structure to the operative portion 160 described above. In some embodiments, the operative portion 160 of the capture portion 340 is the same as or similar in both function and structure to the operative portion 60 described above. In some embodiments, the operative portion 160 can be housed within a working channel of the endoscope 50. In some embodiments, the operative portion 160 can be housed within the capture portion 340.

Figure 10A:
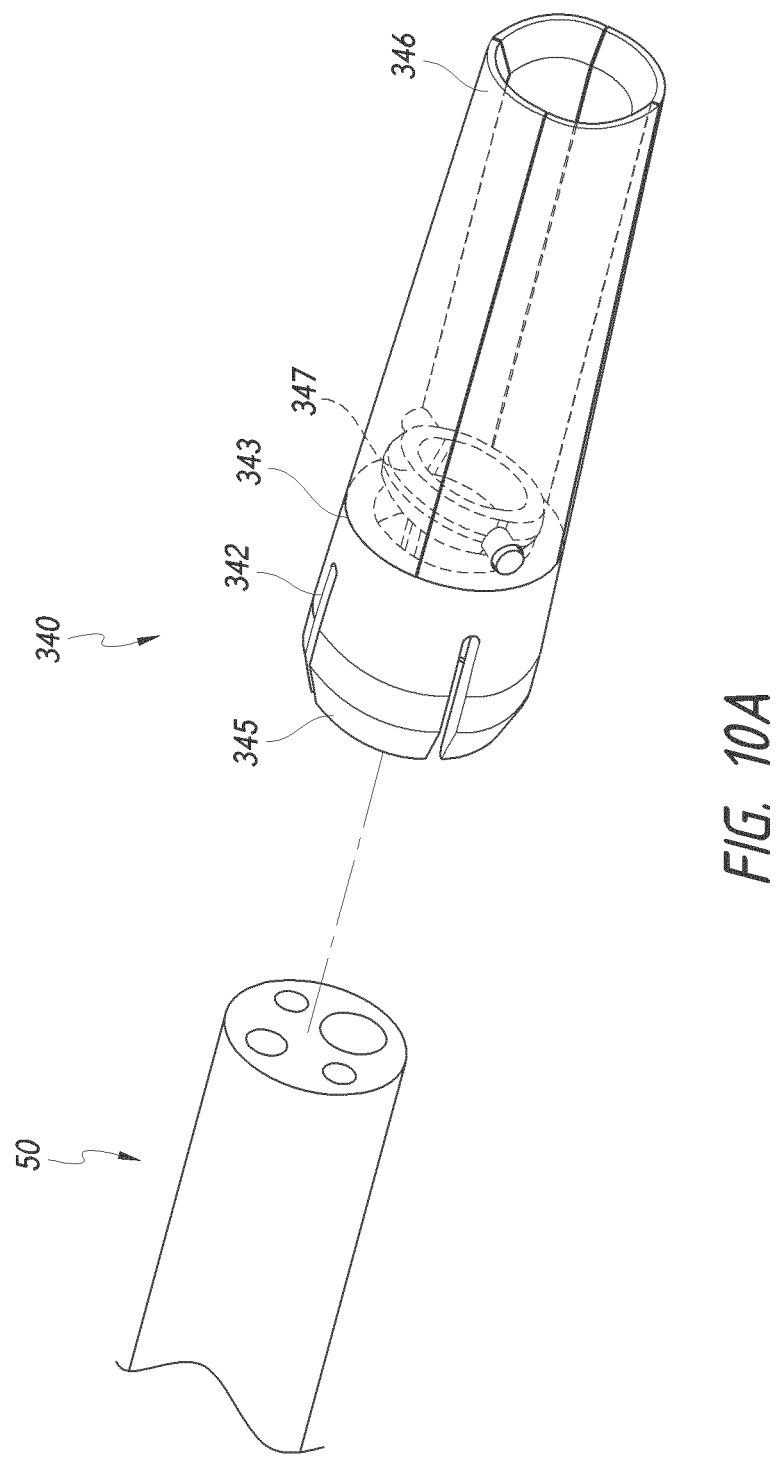
FIG. 10A is a view of a tool configured to be detachable from the distal end of an endoscope.

A method of using the tool illustrated in FIGS. 10A-10E to remove and/or reposition a foreign body (e.g., a medical device 10) can include attaching the proximal end 345 of the capture portion 340 to the distal end of the endoscope 50, as illustrated in FIG. 10A. In some embodiments, the method then can include guiding the capture portion 340 to the site of a medical valve 10, as illustrated in FIG. 10B. In some embodiments, the method can include expanding the compression members 346 to the expanded configuration via rotation of the central ring 347 or through application of other forces upon the compression members 346. In some embodiments, expansion of the compression members 346 can expand the tissue in the vicinity of the capture portion 340. Expansion of the tissue in the vicinity of the capture portion 340 can help to disengage the medical valve 10 from the surrounding tissue (e.g., disengage hyperplastic tissue from the medical valve 10). In some embodiments, the one or more compression members 346 can be fixed in the expanded configuration.

In some embodiments, the method can further include using the operative portion 160 of the capture portion 340 to grab the cap 16 of the medical device 10 in a manner similar to that described above. The operative portion 160 then can be used to pull the medical device 10 in the proximal direction toward the endoscope 50, as illustrated in FIG. 10D. In some embodiments, the operative portion 160 can be used to hold the medical device 10 stable as the capture portion 340 is transitioned toward the medical device 10. As the medical device 10 is approaches the endoscope 50, the struts 24 and/or membrane portion 22 of the medical device 10 can come into contact with the compression members 346. Such contact, as the medical device 10 is pulled toward the endoscope 50, can cause the valve portion 20 to transition to a compressed configuration. In some embodiments, the medical device 10 can be pulled in the proximal direction such that the anchors 31 come into contact with the compression members 346. Such contact can facilitate transition of the anchors 31 from the expanded configuration to the compressed configuration. In some embodiments, the entirety of the medical device 10 can be pulled into the capture portion 340. In some embodiments, the compression members 346 then can be transitioned to a compressed configuration, as illustrated in FIG. 10E. In some embodiments, the one or more compression members 346 can remain in the expanded configuration. In some embodiments, the endoscope 50 then can be used to remove the capture portion 340 and medical device 10 from the patient.

In some embodiments, the endoscope 50 can be used to navigate the capture portion 340 and medical device 10 to another location within the patient's body. In some embodiments, the compression members 346 then can be transitioned to the expanded configuration. The operative portion 160 then can be used to push the medical device 10 in the distal direction out from the capture portion 340. In some embodiments, the compression members 346 can be moved in the proximal direction with respect to the operative portion 160. The medical device 10 then can transition to an expanded configuration and can engage with the tissue surrounding the medical device 10. The operative portion 160 then can be transitioned to the opened configuration to release the medical device 10 from the tool for removing and/or repositioning medical devices. In some embodiments, the endoscope 50 then can be used to navigate the capture portion 340 out of the patient's body.

Although the tool for removing and/or repositioning medical devices has been disclosed in the context of certain embodiments and examples, those skilled in the art will understand that the present disclosure extends beyond the specifically disclosed embodiments to other alternative embodiments and/or uses of the tool and obvious modifications and equivalents thereof. In addition, while several variations of the tool have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of this disclosure. It should be understood that various features and aspects of the disclosed embodiments can be combined with, or substituted for, one another in order to form varying modes or embodiments of the tool. Thus, it is intended that the scope of the present disclosure should not be limited by the particular disclosed embodiments described above.

What is claimed is:

1. A tool for removing and/or repositioning a foreign body within the body of a patient, the tool comprising:
   a sleeve member, the sleeve member having a proximal end, a distal end, and a central axis, the sleeve member comprising:
      a tubular body defining a primary interior lumen; and
      a plurality of secondary conduits longitudinally located within the tubular body,
      wherein the tubular body comprises:
         a distal surface having a primary port for accessing the primary interior lumen and a plurality of secondary ports, wherein each of the secondary ports provides access to a respective one of the secondary conduits,
      the sleeve member being movable in the proximal and distal directions;

a plurality of compression wires having a proximal end and a distal end, the compression wires configured to transition between an expanded configuration, whereby a distal portion of each compression wire is exposed outside of the respective secondary conduit and a compressed configuration, whereby the distal portion is within the conduit, the compression wires further configured to flare outward from the central axis of the sleeve member when in the expanded configuration, such that the distal ends of the compression wires is located further from the central axis than the proximal ends of the compression wires located within the respective secondary conduit, and wherein the compression wires are further configured to be movable in the proximal and distal directions with respect to the sleeve member; and an operative portion, the operative portion having a proximal end and a distal end and a central axis generally coaxial with the central axis of the sleeve member, the operative portion comprising:

a stabilizing portion, the stabilizing portion having a proximal end and a distal end;

a plurality of engagement members, each engagement member having a proximal end and a distal end, the plurality of engagement members connected to the stabilizing portion and extending in the distal direction from the distal end of the stabilizing portion, the engagement members configured to transition between an opened configuration and a closed configuration in response to force applied on the engagement members, the distal ends of the engagement members configured to move away from the central axis of the operative portion when transitioning from the closed configuration to the opened configuration; and one or more grasping portions located on the stabilizing portion, the one or more grasping portions extending from the engagement members toward the central axis of the operative portion when the engagement members are in the closed configuration, wherein the engagement members comprise an indentation section configured to reduce the force required to transition the engagement members between the opened configuration and the closed configuration, wherein the indentation section is located at the proximal end of the engagement members and connects to the distal end of the stabilizing portion, the indentation section has a cross-sectional value that is less than a cross-sectional value of the distal end of the stabilizing portion, wherein the operative portion is moveable relative to the sleeve member.

2. The tool of claim 1, wherein the engagement members are removable from the stabilizing portion.

3. The tool of claim 1, wherein the sleeve member and the operative portion are configured to be moveably housed within a working channel of an endoscope or other deployment device.

4. The tool of claim 1, wherein at least a portion of the operative portion is housed within the interior lumen of the sleeve member.

5. The tool of claim 1, wherein the engagement members are biased to the opened configuration.

6. The tool of claim 1, wherein at least one of the compression wires is biased to the expanded configuration.

7. The tool of claim 1, wherein the engagement members are configured to transition from the opened configuration to the closed configuration when the distal end of the sleeve member is moved from proximal to the proximal ends of the engagement members to lateral or distal to the distal ends of the engagement members.

8. The tool of claim 1, wherein each engagement member is configured to come into contact with each other when the operative portion is in a closed configuration.

9. The tool of claim 1, wherein a gap is formed between the plurality of engagement members over at least a portion of the axial length of the engagement members when the engagement members are in the closed configuration.

10. The tool of claim 9, wherein the foreign body comprises an extended portion and a central axis such that, when the central axis of the foreign body is not aligned with the central axis of the operative portion, the extended portion can pass through the gap formed between the engagement members and the grasping portions can grasp the sides of the extended portion.

11. The tool of claim 1, wherein the foreign body comprises a valve portion having a membrane portion with an open proximal end and a closed distal end, wherein the proximal ends of the compression wires are configured to engage with the open proximal end of the membrane portion of the valve portion before engaging with the closed distal end.

12. The tool of claim 1, wherein at least one of the compression wires comprises Nitinol.

13. A tool for repositioning or removing a foreign body within the body of a patient, the tool comprising:

a capture portion having a proximal end and a distal end and a central axis, the capture portion comprising:

a body portion having a distal end and a proximal end, the body portion located on the proximal end of the capture portion, the proximal end of the body portion configured to removably connect to an endoscope, the body portion being formed around a central lumen, wherein the body portion comprises a plurality of secondary conduits and a distal surface comprising:

a primary port for accessing the central lumen; and a plurality of secondary ports, wherein each of the secondary ports provides access to a respective one of the secondary conduits;

a plurality of compression wires, each of the compression wires configured to be slidably received within one of the secondary conduits, wherein at least one of the compression wires is in an expanded configuration when a distal end of the compression wire is located distal from the respective secondary port, wherein the at least one of the compression wires is in a retracted configuration when the distal end of the compression wire is located within the respective secondary conduit; and an operative portion configured to transition between a closed configuration and an opened configuration, the operative portion further configured to grasp a portion of the foreign body when the operative portion is transitioned from the opened configuration to the closed configuration while a portion of the foreign body is within the operative portion, the operative portion further configured to be housed within a working channel of the endoscope, wherein the operative portion comprises:

a proximal end;

a distal end; and at least one indentation located between the proximal end and the distal end, wherein the at least one indentation is configured to reduce the force required to transition the operative portion between the opened configuration and the closed configuration, the indentation comprises a cross-sectional value that is less than a cross-sectional value of the proximal end of the operative portion, wherein the operative portion is moveable relative to the body portion.

14. The tool of claim 13, wherein the one or more compression wires are configured to transition between the retracted configuration and the expanded configuration upon the application of a force upon the one or more compression wires.

* * * * *